United States Patent
Kato et al.

(10) Patent No.: US 9,757,344 B2
(45) Date of Patent: Sep. 12, 2017

(54) FINE PARTICLES COATED WITH LIPID MEMBRANE

(75) Inventors: Yasuki Kato, Sunto-gun (JP);
Masahiro Yamauchi, Sunto-gun (JP);
Hiroko Kusano, Sunto-gun (JP);
Takeshi Iwata, Sunto-gun (JP);
Takaaki Uochi, Sunto-gun (JP); Shiro Akinaga, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 12/656,487

(22) Filed: Feb. 1, 2010

(65) Prior Publication Data

US 2010/0166847 A1    Jul. 1, 2010

Related U.S. Application Data

(62) Division of application No. 10/398,222, filed as application No. PCT/JP01/08759 on Oct. 4, 2001, now Pat. No. 7,678,415.

(30) Foreign Application Priority Data

Oct. 4, 2000   (JP) ................................ 2000/305065

(51) Int. Cl.
    *A61K 9/19*     (2006.01)
    *A61K 9/64*     (2006.01)
    (Continued)

(52) U.S. Cl.
    CPC ............ *A61K 9/5123* (2013.01); *A61K 9/127* (2013.01); *A61K 9/1271* (2013.01);
    (Continued)

(58) Field of Classification Search
    CPC ........ A61K 9/127; A61K 9/141; A61K 9/146; A61K 9/513
    (Continued)

(56) References Cited

U.S. PATENT DOCUMENTS 4,794,000 A   12/1988   Ecanow
4,914,084 A    4/1990   Ecanow
(Continued)

FOREIGN PATENT DOCUMENTS

EP   0 275 358     7/1988
JP   63-239213    10/1988
(Continued)

OTHER PUBLICATIONS

F. Martin et al., Stealth Liposomes, CRC Press Inc., Florida, pp. 93-102, 1995.
(Continued)

*Primary Examiner* — Holly Le
(74) *Attorney, Agent, or Firm* — Wenderoth, Lind & Ponack, L.L.P.

(57) ABSTRACT

A coated fine particle comprisisng: (i) a complex of a drug and a cationic lipid, wherein (a) the drug is a nucleic acid and the complex is obtained by mixing the drug and the cationic lipid in water, wherein the complex has a diameter of 10 nm to 1,000 nm, and (ii) a lipid layer formed of lipid(s), wherein the lipid(s) is selected from phospholipid, glyceroglycolipid, sphingoglycolipid, cholesterol and synthetic lipid, wherein the complex is coated with the lipid layer.

1 Claim, 3 Drawing Sheets

(51) Int. Cl.
| | |
|---|---|
| A61K 9/51 | (2006.01) |
| A61K 9/14 | (2006.01) |
| A61K 9/127 | (2006.01) |
| A61K 9/50 | (2006.01) |
| B01J 13/12 | (2006.01) |
| A61K 31/7088 | (2006.01) |
| A61K 47/48 | (2006.01) |

(52) U.S. Cl.
CPC ............ *A61K 9/1272* (2013.01); *A61K 9/141* (2013.01); *A61K 9/146* (2013.01); *A61K 9/5015* (2013.01); *A61K 9/5192* (2013.01); *A61K 31/7088* (2013.01); *A61K 47/48815* (2013.01); *B01J 13/12* (2013.01)

(58) Field of Classification Search
USPC .... 436/13, 86; 424/474, 475, 477, 490, 491, 424/498; 428/403, 407
See application file for complete search history.

(56) References Cited

U.S. PATENT DOCUMENTS

| | | | |
|---|---|---|---|
| 4,943,449 | A | 7/1990 | Aishima et al. |
| 5,000,887 | A | 3/1991 | Tenzel et al. |
| 5,049,392 | A * | 9/1991 | Weiner et al. ................ 424/450 |
| 5,077,056 | A | 12/1991 | Bally et al. |
| 5,100,591 | A | 3/1992 | Leclef et al. |
| 5,316,771 | A | 5/1994 | Barenholz et al. |
| 5,542,935 | A | 8/1996 | Unger et al. |
| 5,770,222 | A * | 6/1998 | Unger et al. .................. 424/450 |
| 5,795,587 | A | 8/1998 | Gao et al. |
| 5,955,575 | A | 9/1999 | Peri et al. |
| 5,981,501 | A | 11/1999 | Wheeler et al. |
| 6,090,800 | A * | 7/2000 | Unger ................ A61K 41/0028 514/180 |
| 6,120,751 | A * | 9/2000 | Unger ................ A61K 41/0028 264/4 |
| 6,211,162 | B1 | 4/2001 | Dale et al. |
| 6,248,722 | B1 * | 6/2001 | Morishita et al. .......... 514/44 R |
| 6,426,086 | B1 * | 7/2002 | Papahadjopoulos et al. 424/450 |
| 6,936,215 | B1 | 8/2005 | Price et al. |
| 7,071,293 | B1 | 7/2006 | Tack et al. |
| 7,381,421 | B2 * | 6/2008 | Gregoriadis ................... 424/450 |
| 7,678,415 | B2 * | 3/2010 | Kato et al. ................. 427/213.3 |
| 2001/0038851 | A1 * | 11/2001 | Allen et al. .................... 424/450 |
| 2003/0134420 | A1 | 7/2003 | Lollo et al. |

FOREIGN PATENT DOCUMENTS

| | | |
|---|---|---|
| JP | 01294626 | 11/1989 |
| JP | 3-218309 | 9/1991 |
| JP | 03-218309 | 9/1991 |
| JP | 04-244017 | 9/1992 |
| WO | 90/04384 | 5/1990 |
| WO | 96/40964 | 12/1996 |
| WO | 98/51278 | 11/1998 |
| WO | 99/18933 | 4/1999 |
| WO | 00/51565 | 9/2000 |

OTHER PUBLICATIONS

D. Litzinger et al., "Fate of cationic liposomes and their complex with oligonucleotide in vivo", Biochimica et Biophysica Acta, 1281, pp. 139-149, 1996.
C. Bennett et al., "Pharmacokinetics in mice of a [$^3$H]-labeled phosphorothioate oligonucleotide formulated in the presence and absence of a cationic lipid", Journal of Controlled Release, 41, pp. 121-130, 1996.
S. Li et al., "Characterization of cationic lipid-protamine-DNA (LPD) complexes for intravenous gene delivery", Gene Therapy, 5, pp. 930-937, 1998.
S. Li et al., "Dynamic changes in the characteristics of cationic lipidic vectors after exposure to mouse serum: implications for intravenous lipofection", Gene Therapy, 6, pp. 585-594, 1999.
O. Meyer et al., "Cationic Liposomes coated with polyethylene glycol as carriers for oligonucleotides", The Journal of Biological Chemistry, vol. 273, No. 25, Jun. 19, 1998, pp. 15621-15627.
D. Stuart et al., "A new liposomal formulation for antisense oligodeoxynucleotides with small size, high incorporation efficiency and good stability", Biochimica et al Biophysica Acta, 1463, pp. 219-229, 2000.
D. McPhail et al., "Liposomes encapsulating polymeric chitosan based vesicles—a vesicle in vesicle system for drug delivery", International Journal of Pharmaceutics, 200, pp. 73-86, 2000.
A. Bangham et al., "Diffusion of univalent ions across the lamellae of swollen phospholipids", J. Mol. Biol., 13, pp. 238-252, 1965.
S. Batzri et al., "Interaction of phospholipid vesicles with cells", The Journal of Cell Biology, 66, pp. 621-634, 1975.
Y. Barenholtz et al., FEBS Letters, vol. 99, No. 1, pp. 210-214, 1979.
U. Pick, "Liposomes with a large trapping capacity prepared by freezing and thawing of sonicated phospholipid mixtures", Archives of Biochemistry and Biophysics, vol. 212, No. 1, Nov. 1981, pp. 186-194.
F. Szoka et al., "Procedure for preparation of liposomes with large internal aqueous space and high capture by reverse-phase evaporation", Proc. Natl. Acad. Sci. USA, vol. 75, No. 9, Sep. 1978, pp. 4194-4198.
S. Hwang et al., "Remote loading of diclofenac, insulin and fluorescein isothiocyanate labeled insulin into liposomes by pH and acetate gradient methods", International Journal of Pharmaceutics, 179, pp. 85-95, 1999.
P. Felgner et al., "Lipofection: A highly efficient, lipid-mediated DNA-transfection procedure", Proc. Natl. Acad. Sci. USA, vol. 84, pp. 7413-7417, Nov. 1987.
J. Behr et al., "Efficient gene transfer into mammalian primary endocrine cells with lipopolyamine-coated DNA", Proc. Natl. Acad. Sci. USA, 86, pp. 6982-6986, 1989.
J. Felgner et al., "Cationic lipid-mediated delivery of polynucleotides", Methods, 5, pp. 67-75, 1993.
X. Gao et al., "A novel cationic liposome reagent for efficient transfection of mammalian cells", Biochemical and Biophysical Research Communications, vol. 179, No. 1, Aug. 30, 1991, pp. 280-285.
R. Muller et al., "Emulsions and Nanosuspensions for the formulation of poorly soluble drugs", High-pressure homogenization techniques for the production of liposome dispersions: potential and limitations, pp. 267-294, 1998.
J. Wheeler et al., "Stabilized plasmid-lipid particles: construction and characterization", Gene Therapy, 6, pp. 271-281, 1999.
Ishii, F. et al., *Procedure for Preparation of Lipid Vesicles (Liposomes) Using the Coacervation (Phase Separation) Technique*, Langmuir, vol. 11, No. 2 (1995), pp. 483-486.
Ishii, F. et al., *Characteristics and Development of the Special Functions of Liposomes*, Membrane, vol. 23, No. 1 (1998), pp. 23-30 (corresponds to CU).
International Search Report dated Dec. 18, 2001 in International (PCT) Application No. PCT/JP01/08759.

* cited by examiner

FINE PARTICLES COATED WITH LIPID MEMBRANE

This application is a divisional of U.S. application Ser. No. 10/398,222, filed Jul. 3, 2003, which has matured to U.S. Pat. No. 7,678,415, issued Mar. 16, 2010, and which was a national stage application of International application No. PCT/JP01/08759, filed Oct. 4, 2001.

TECHNICAL FIELD

The present invention relates to a method for coating fine particles with lipid membrane.

BACKGROUND ART

It has widely known that a drug is enclosed in fine particles to enhance the effect of the drug, and that the fine particles include, for example, liposome, fat emulsion, etc. Their clinical applications are carried out mainly by injections, particularly by intravascular administration. The fine particles administered to blood vessel have been known to interact with blood components and, as a result of the interaction, the fine particles themselves or the drug is destructed (disintegrated), or the fine particles are opsonized whereupon they are removed from the blood (they are removed as an extraneous substance by a reticuloendothelial system). In order to prevent that removal, modification of liposome with polyethylene glycol, for example, has been studied [Stealth Liposomes, ed. by D. D. Lasic and F. Martin, CRC Press Inc., Florida, 93-102 (1995)].

Further, in order to deliver a nucleic acid such as oligonucleotide, DNA and RNA to target cells, a complex of a nucleic acid with liposome comprising lipid containing cationic lipid (hereinafter, referred to as cationic lipid liposome), a basic polymer such as poly-L-lysine and polyamideamine have been frequently used. However, it has been known that, when a complex of cationic lipid liposome with a nucleic acid is intravenously administered, it is quickly distributed from blood to liver, lung, etc. [Biochim. Biophys. Acta, 1281, 139-149 (1996) ; J. Controlled Release, 41, 121-130 (1996)]. On the other hand, S. Li, et al. has reported that, when mouse serum is contacted with a cationic lipid liposome/DNA complex, an increase in the size of the complex, aggregation, disintegration of liposome, and release and disintegration of DNA has taken place [Gene Therapy, 5, 930-937 (1998); Gene Therapy, 6, 585-594 (1999)]. In order to solve those problems, modification of cationic lipid liposome with polyethylene glycol was studied, and O. Meyer, et al. prepared a complex of oligodeoxynucleotide (ODN) with cationic lipid liposome containing polyethylene glycol phosphatidylethanolamine (PEG-PE) [J. Biol. Chem., 273, 15621-15627 (1998)]. However, when it was contacted with a 50% aqueous solution of human plasma for 4 hours, 35% of ODN were dissociated. In order to reduce the dissociation, D. Stuart and T. Allen previously dissolved the cationic lipid liposome in chloroform, mixed the resulting solvent with an aqueous ODN solution and methanol, and transferred a cationic lipid liposome/ODN complex to chloroform layer, and subjecting to centrifugal separation. They further took out the chloroform layer, added thereto PEG lipid, neutral lipid and water to form W/O emulsion. They have tried to enclose ODN inside the liposome completely by forming the W/O emulsion in a manner similar to a reverse phase evaporation method of F. Szoka, et al. [Biochim. Biophys. Acta, 1463, 219-229 (2000)]. In recent years, however, the use of chloroform is not considered to be desirable in view of safety. Further, D. McPhail, et al. prepared a vesicle-in-vesicle where chitosan vesicle is placed in liposome by adding a vesicle suspension (chitosan vesicle) of palmitoyl-chitosan and cholesterol to a thin layer of egg yolk phosphatidylcholine and cholesterol [Int. J. Pharmaceutics, 200, 73-86 (2000)]. However, there is no description about the enclosing efficiency and, when guessed from the preparation method, the enclosing efficacy was presumed to be as low as about a few percent, which is presumed to cause a problem in its practical use. From such viewpoints as well, convenient and highly efficient enclosure of fine particles by closed vesicle is very useful when application to medical treatment is aimed.

Further, there are some cases where many peptides and proteins which are useful in medical care are quickly decomposed in living body by enzyme or the like or are removed from living body as a result of generation of an antibody by frequent administrations, whereby their effect is no longer exerted. Therefore, with an object of enhancing the stability of those peptides and proteins in living body, it has been attempted to enclose them into liposome. As the means of enclosing them into liposome, there have been known, for example, a liposome preparation method by Bangham, et al. [J. Mol. Biol., 13, 238 (1965)], an ethanol injection method [J. Cell Biol., 66, 621 (1975)], a French press method [FEBS Lett., 99, 210 (1979)], a freeze-thaw method [Arch. Biochem. Biophys., 212, 186 (1981)], a reverse phase evaporation method [Proc. Natl. Acad. Sci. USA, 75, 186 (1981)], a pH gradient method (Japanese Patent No. 2,572,554; Japanese Patent No. 2,659,136; etc.) and the like. For low-molecular compounds, a pH gradient method is appropriate and improved method thereof has been devised as well. However, with regard to peptides and proteins, invariably efficient enclosing has not been achieved yet and, in the case of fluorescence-labeled insulin, it was enclosed to an extent of about 5 to 40% but no insulin was enclosed at all [Int. J. Pharmaceutics, 179, 85-95 (1999)]. In order to enhance the therapeutic effect by peptides and proteins, it is in demand to develop a method whereby peptides and proteins are efficiently enclosed within closed vesicles.

BRIEF SUMMARY OF THE INVENTION

An object of the present invention is to provide a safe, convenient and efficient method for coating fine particles with lipid membrane in order to stabilize a drug etc. contained in the said fine particles. When the fine particles are enclosed in closed vesicles comprising lipid bilayer or multilayer membrane using the said coating method, affection by components in living body particularly in blood or in gastrointestinal tract and by reticuloendothelial system and also affection during storage period by each of the fine particles or by a dispersing medium wherein the fine particles are dispersed can be suppressed.

The present inventors have found that a complex comprising a water-soluble drug and cationic lipid formed due to electrostatic interaction is not soluble in an aqueous solution of ethanol and that, although phospholipid is soluble in an aqueous solution of ethanol having a high concentration of ethanol, it forms a liposome due to formation of lipid membrane in an aqueous solution of ethanol having a low concentration of ethanol. As a result of further intensive investigations, it has been found that a complex of a drug with lipid can be coated with a lipid membrane comprising polyethylene glycolated lipid and phospholipids, when a water-soluble polymer derivative such as polyethylene glycolated lipid is previously added to a complex of a water-soluble drug with lipid, the mixture is dispersed in an aqueous solution of ethanol having a high concentration of ethanol, polyethylene glycolated lipid and phospholipid are dissolved in the resulting liquid and then the content of ethanol is gradually reduced.

BRIEF DESCRIPTION OF THE DRAWINGS

FIG. 1 also shows the complex with closed vesicles of a lipid bilayer obtained in Examples 7 to 18. Examples 7-13 and 17 utilize PEG-DSPE for the lipid bilayer, while Examples 14, 15, 16 and 18 use polyoxyethylene hydrogenated castor oil 60, CREMOPHOR and Tween 80 in place of PEG-DSPE for the lipid bilayer.

Symbols used in FIG. 2 to FIG. 5 have the following meanings.

Figure 1:
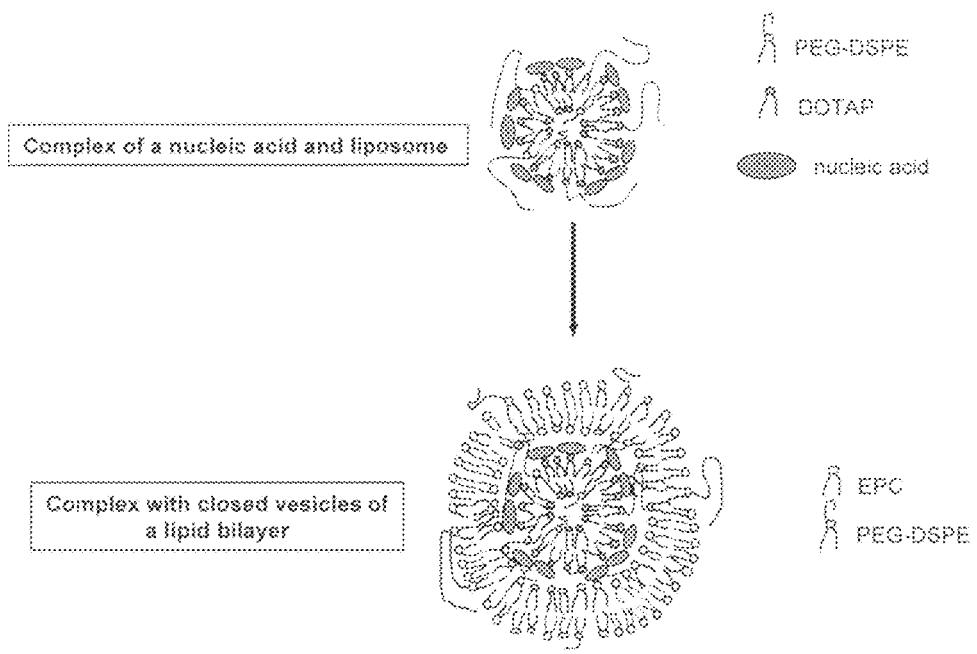
FIG. 1 shows a complex of a nucleic acid and a liposome.
Figure 2:
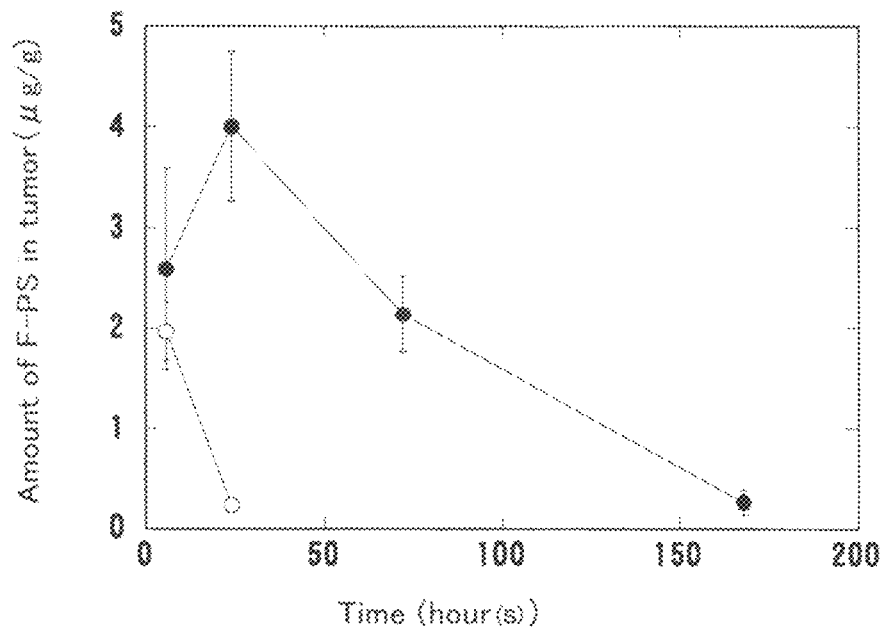
FIG. 2 shows the amount of F-PS distributed to tumor. Abscissa shows time (hour(s)) after, administration of the preparation, while ordinate shows the amount of F-PS in tumor.
Figure 3:
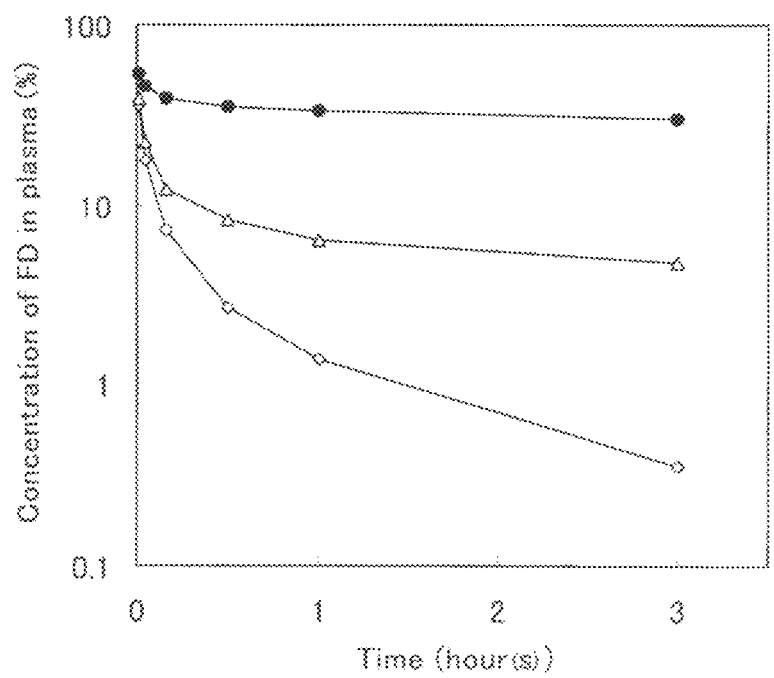
FIG. 3 shows the concentration of FD in plasma. Abscissa shows time (hour(s)) after administration of the preparation, while ordinate shows the concentration of FD in plasma.
Figure 4:
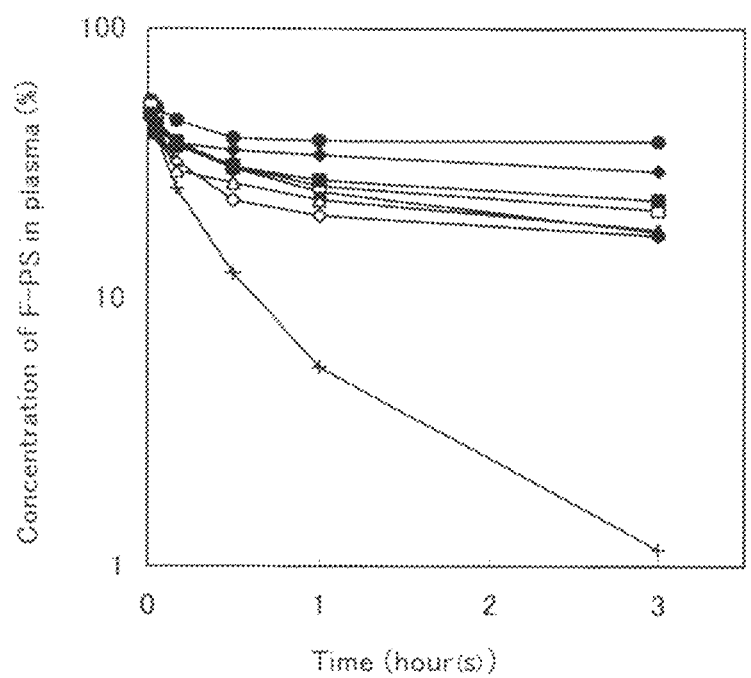
FIG. 4 shows the concentration of F-PS in plasma. Abscissa shows time (hour(s)) after administration of the preparation, while ordinate shows the concentration of F-PS in plasma.
Figure 5:
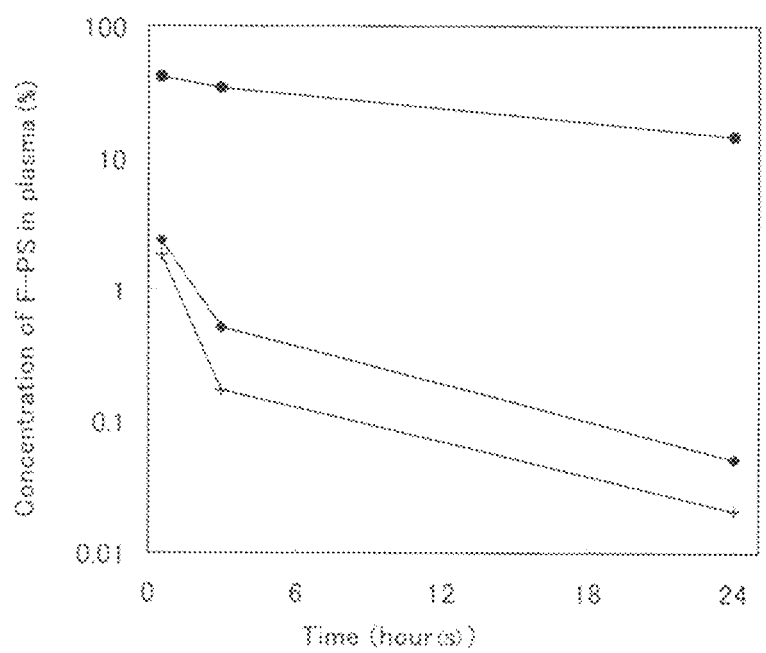
FIG. 5 shows the concentration of F-PS in plasma. Abscissa shows time (hour(s)) after administration of the preparation, while ordinate shows the concentration of F-PS in plasma.

FIG. 2
-●-: group to which the preparation 7 was administered
-○-: group to which the preparation f was administered FIG. 3
-●-: group to which the preparation 1 was administered
-◇-: group to which the preparation a was administered
-Δ-: group to which the preparation b was administered FIG. 4
-●-: group to which the preparation 7 was administered
-◇-: group to which the preparation 8 was administered
-◆-: group to which the preparation 9 was administered
-Δ-: group to which the preparation 10 was administered
-▲: group to which the preparation 11 was administered
-□-: group to which the preparation 12 was administered
-■-: group to which the preparation 13 was administered
-+-: group to which the preparation f was administered FIG. 5
-●-: group to which the preparation 7 was administered
-+-: group to which the preparation f was administered
-◆-: group to which the preparation g was administered

DETAILED DESCRIPTION OF THE INVENTION

Thus, the present invention relates to the following (1) to (19).

(1) A method for coating fine particles with lipid membrane, which comprises coating fine particles with lipid membrane by decreasing the rate of a polar organic solvent in an aqueous solution containing the polar organic solvent where the fine particles are dispersed and lipid is dissolved.

(2) A method for coating fine particles with lipid membrane, which comprises coating fine particles with lipid membrane by dispersing fine particles in an aqueous solution containing a polar organic solvent (liquid A), dissolving lipid in a polar organic solvent or an aqueous solution containing a polar organic solvent which is the same as or different from the above aqueous solution containing a polar organic solvent (liquid B), mixing the liquid A and the liquid B into liquid C, and decreasing the rate of a polar organic solvent in the liquid C to obtain liquid D.

(3) The method for coating fine particles with lipid membrane according to the above (2), wherein the liquid B is a solution which is prepared by dissolving a water-soluble polymer derivative (I) together with the lipid.

(4) The method for coating fine particles with lipid membrane according to the above (2) or (3), wherein the concentrations of the polar organic solvent in the liquid A and the liquid B are 30% or more.

(5) The method for coating fine particles with lipid membrane according to the above (2) or (3), wherein the concentrations of the polar organic solvent in the liquid A and the liquid B are 60 to 90%.

(6) The method for coating fine particles with lipid membrane according to the above (5), wherein the concentration of the polar organic solvent in the liquid D is 50% or less.

(7) The method for coating fine particles with lipid membrane according to any one of the above (1) to (6), wherein the fine particles are those containing a water-soluble polymer derivative which is the same as or different from the water-soluble polymer derivative (I) recited in the above (3).

(8) The method for coating fine particles with lipid membrane according to any one of the above (1) to (7), wherein the fine particles are those containing one or more member (s) selected from a drug, lipid assembly, liposome, fine particles in the emulsion, natural polymer, synthetic polymer, metal colloid, cationic lipid, anionic lipid and a fine particle preparation.

(9) The method for coating fine particles with lipid membrane according to any one of the above (1) to (7), wherein the fine particles are those containing a drug.

(10) The method for coating fine particles with lipid membrane according to any one of the above (1) to (7), wherein the fine particles comprise a complex of a drug with one or more member(s) selected from lipid assembly, liposome, fine particles in the emulsion, natural polymer, synthetic polymer, metal colloid, cationic lipid, anionic lipid and a fine particle preparation.

(11) The method for coating fine particles with lipid membrane according to any one of the above (1) to (7), wherein the fine particles comprise a complex of a drug with cationic lipid.

(12) The method for coating fine particles with lipid membrane according to any one of the above (1) to (7), wherein the fine particles comprise a complex of a drug with anionic lipid.

(13) The method for coating fine particles with lipid membrane according to any one of the above (1) to (7), wherein the fine particles comprise a complex of a drug, liposome containing phospholipid and a dextran sulfate sodium salt.

(14) The method for coating fine particles with lipid membrane according to anyone of the above (8) to (13), wherein the drug is a drug selected from a peptide, a protein, a nucleic acid, a low-molecular compound, a saccharide and a polymer compound.

(15) The method for coating fine particles with lipid membrane according to anyone of the above (1) to (14), wherein the polar organic solvent is one or more, member(s) selected from an alcohol, a glycol and a polyalkylene glycol.

(16) The method for coating fine particles with lipid membrane according to the above (15), wherein the alcohol is ethanol.

(17) The method for coating fine particles with lipid membrane according to the above (15) or (16), wherein the glycol is a propylene glycol.

(18) The method for coating fine particles with lipid membrane according to anyone of the above (15) to (17), wherein the polyalkylene glycol is polyethylene glycol.

(19) The method for coating fine particles with lipid membrane according to anyone of the above (3) to (18), wherein the water-soluble polymer derivative is one or more member(s) selected from polyethylene glycolated lipid, a polyethylene glycol alkyl ether, a polyethylene glycol castor oil derivative, a polyethylene glycol sorbitan fatty acid ester, a polyethylene glycol stearate, a copolymer of ethylene glycol with propylene glycol and a glycerol ester.

Examples of the polar organic solvent in the aqueous solution containing the polar organic solvent used in the present invention are an alcohol such as methanol, ethanol, n-propanol, isopropanol, n-butanol, isobutanol and tert-butanol; a glycol such as glycerol, ethylene glycol and propylene glycol; and polyalkylene glycol such as polyethylene glycol.

With regard to the thing which constitutes the fine particles used in the present invention, there is no particular limitation and its examples are a drug, lipid assembly, liposome, fine particles in emulsion, natural polymer, synthetic polymer, metal colloid, cationic lipid, anionic lipid, a fine particle preparation and a water-soluble polymer derivative. They may be used independently, as a complex where two or more of them are combined, or as a complex where one or more of them and another compound are combined.

To be specific, an example of the above-mentioned complex is a complex of drug with one or more member(s) selected from lipid assembly, liposome, fine particles in emulsion, natural polymer, synthetic polymer, metal colloid, cationic lipid, anionic lipid and a fine particle preparation and, to be more specific, it is a complex of a nucleic acid with cationic lipid formed due to electrostatic interaction; a complex of a nucleic acid with positive-charged polymer such as poly-L-lysine; a complex of a basic protein having a high isoelectric point with anionic lipid such as phosphatidic acid or negative-charged polymer such as styrene-maleic acid; a complex of an acidic protein with positive-charged polymer such as cationic lipid and poly-L-lysine; etc.

With regard to the drug, its examples are substances having a pharmacological activity such as a protein including enzyme, a peptide, a nucleic acid including gene, a low-molecular compound, a saccharide and a polymer compound. Examples of the protein including enzyme and the peptide are bradykinin, angiotensin, oxytocin, vasopressin, adrenocorticotropin (ACTH), calcitonin, insulin, glucagon, cholecystokinin, β-endorphin, melanocyte inhibiting factor, melanocyte stimulating hormone, gastrin antagonist, neurotensin, somatostatin, brucine, cyclosporine, enkephalin, transferrin, RGD (Arg-Gly-Asp) peptide, thyroid hormone, growth hormone, gonadotropic hormone, luteinizing hormone (LHRH), asparaginase, arginase, uricase, carboxypeptidase, glutaminase, superoxide dismutase (SOD), tissue plasminogen activator (t-PA), streptokinase, interleukin, interferon, muramyl dipeptide, thymopoietin, granulocyte colony stimulating factor (G-CSF), granulocyte macrophage colony stimulating factor (GM-CSF), erythropoietin (EPO), thrombopoietin (TPO), trypsin inhibitor, lysozyme, epidermal growth factor (EGF), insulin-like growth factor (IGF), nerve growth factor (NGF), platelet-derived growth factor (PDGF), transforming growth factor (TGF), endothelial cell growth factor (ECGF), fibroblast growth factor (FGF), glial growth factor (GGF), thymosin and a specific antibody (such as anti-EGF receptor antibody); examples of the nucleic acid including gene are nucleic acids such as antisense oligonucleotide, sense oligonucleotide, DNA and RNA; examples of the low-molecular compound are ε-aminocaproic acid, arginine hydrochloride, potassium L-aspartate, tranexamic acid, bleomycin sulfate, vincristine sulfate, cefazolin sodium, cephalothin sodium, citicoline, cytarabine, gentamicin sulfate, vancomycin hydrochloride, kanamycin sulfate and amikacin sulfate; examples of the saccharide are sodium chondroitin sulfate, heparin sodium and dextran fluorescein; and examples of the polymer compound are sodium polyethylene sulfonate, DIVEMA (copolymer of divinyl ether with maleic anhydride) and SMANCS (bonded product of a styrene-maleic anhydride copolymer with neocarzinostatin).

Examples of the lipid assembly are spherical micelle, spherical reversed micelle, sausage-shaped micelle, sausage-shaped reversed micelle, plate-shaped micelle, plate-shaped reversed micelle, hexagonal I, hexagonal II and associated product comprising two or more lipid molecules.

Examples of the lipid constituting the liposome are phospholipid, glyceroglycolipid, sphingoglycolipid, cholesterol and cationic lipid, and phospholipid is preferably used. Such lipid may be modified by nonionic detergent such as Polysorbate 80, Pluronic F68 and sorbitan monolaurate (e.g., Span 20); cationic detergent such as benzalkonium chloride; anionic detergent such as sodium lauryl sulfate; polysaccharide such as dextran or a derivative thereof; a polyoxyethylene derivative such as polyoxyethylene lauryl alcohol and polyethylene glycol (PEG); etc.

Examples of the phospholipid are natural or synthetic phospholipids such as phosphatidylcholine (soybean phosphatidylcholine, egg yolk phosphatidylcholine, distearoyl phosphatidylcholine, dipalmitoyl phosphatidylcholine, etc.), phosphatidylethanolamine (distearoyl phosphatidylethanolamine, dipalmitoyl phosphatidylethanolamine, etc.), phosphatidylserine, phosphatidic acid, phosphatidylglycerol, phosphatidylinositol, lysophosphatidylcholine, sphingomyelin, polyethylene glycolated phospholipid, egg yolk lecithin, soybean lecithin and hydrogenated phospholipid.

Examples of the glyceroglycolipid are sulfoxyribosyl glyceride, diglycosyl diglyceride, digalactosyl diglyceride, galactosyl diglyceride and glycosyl diglyceride.

Examples of the sphingoglycolipid are galactosyl cerebroside, lactosyl cerebroside and ganglioside.

Examples of the cationic lipid are 1,2-dioleoyl-3-trimethyl ammonium propane (DOTAP), N-(2,3-dioleyloxypropan-1-yl)-N,N,N-trimethylammonium chloride (DOTMA), 2,3-dioleyloxy-N-[2 (sperminecarboxyamido)ethyl]-N,N-dimethyl-1-propanaminium trifluoroacetate (DOSPA), 1,2-dimyristyloxypropyl-3-dimethylhydroxyethyl ammonium bromide (DMRIE), 1,2-dioleoyloxypropyl-3-diethylhydroxyethylammonium bromide (DORIE) and 3β-[N-(N',N'-dimethylaminoethyl)carbamoyl]-cholesterol (DC-Chol1).

In liposome, those lipids each is used either independently or jointly. When they are used jointly, the lipids used are, for example, lipids comprising at least two components selected from hydrogenated soybean phosphatidylcholine, polyethylene glycolated phospholipid and cholesterol; lipids comprising at least, two components selected from distearoyl phosphatidylcholine, polyethylene glycolated phospholipid and cholesterol; lipids comprising egg yolk phosphatidylcholine and DOTAP; lipids comprising egg yolk phosphatidylcholine, DOTAP and polyethylene glycolated phospholipid; lipids comprising egg yolk phosphatidylcholine, DOTAP, cholesterol and polyethylene glycolated phospholipid; etc.

Further, in the preparation of liposome, sterol or the like such as cholesterol as a membrane stabilizer, tocopherol or the like as an antioxidant and stearylamine, dicetyl phosphate, ganglioside and cationic lipid such as DOTMA [Proc. Natl. Acad. Sci. USA, 84, 7413-7417 (1987)], dioctadecylamidoglycyl spermine (DOGS) [Proc. Natl. Acad. Sci. USA, 86, 6982-6986 (1989)], DMRIE or DORIE [Methods, 5, 67-75 (1993)] and DC-Chol [Biochem. Biophys. Res. Commun., 179, 280-285 (1991)] as a charging substance may also be added, if necessary, together with lipid.

There is no particular limitation for the fine particles in the emulsion, and their specific examples are fine particles contained in all kinds of O/W emulsion and W/O/W emulsion such as a fat emulsion, an emulsion comprising nonionic detergent and soybean oil, a lipid emulsion and a lipid nanosphere.

There is no particular limitation for the natural polymer, and its specific examples are albumin, dextran, chitosan, deoxyribonucleic acid and the like.

There is no particular limitation for the synthetic polymer substance and its specific examples are poly-L-lysine, polyethyleneimine, polyaspartic acid, a copolymer of styrene with maleic acid, a copolymer of isopropylacrylamide with acrylpyrrolidone, PEG-modified dendrimer, polylactic acid, polylactic acid polyglycolic acid, polyethylene glycolated polylactic acid, dextran sulfate and a salt thereof.

Here, the salt includes metal salt, ammonium salt, organic amine addition salt, amino acid addition salt, etc.

Examples of the metal salt are alkaline metal salt such as lithium salt, sodium salt and potassium salt; alkaline earth metal salt such as magnesium salt and calcium salt; aluminum salt; zinc salt; etc. Examples of the ammonium salt are ammonium salt, tetramethylammonium salt, etc.; examples of the organic amine addition salt are addition salts of morpholine, piperidine, etc.; and examples of the amino acid addition salt are addition salts of glycine, phenylalanine, aspartic acid, glutamic acid, lysine, etc.

Examples of the metal colloid are metal colloids containing gold, silver, platinum, copper, rhodium, silica, calcium, aluminum, iron, indium, cadmium, barium, lead, etc.

With regard to the cationic lipid, the same ones as those mentioned above may be exemplified.

Examples of the anionic lipid are phosphatidylserine, phosphatidylglycerol and phosphatidylinositol.

Examples of the fine particle preparation are microsphere, microcapsule, nanocrystal and lipid nanoparticle polymer micelle.

With regard to the fine particles, those where a drug is enclosed in liposome may be preferably exemplified.

With regard to the size of the fine particles, an average particle size thereof is preferably from several nm to several tens μm and, more preferably, from 10 nm to 1,000 nm.

There is no particular limitation for the water-soluble polymer derivative used in the present invention, and its examples are polyethylene glycolated lipid such as PEG-PE, 1,2-distearoyl-sn-glycero-3-phosphatidylethanolamine-N-(polyethyleneglycol 2000) (PEG-DSPE); polyethylene glycol alkyl ether; a polyoxyethylene castor oil derivative such as polyoxyethylene hydrogenated castor oil 60 and Cremophor EL; a polyethylene glycol sorbitan fatty acid ester such as polyoxyethylene sorbitan monooleate (Tween 80); a polyethylene glycol stearic acid ester; a copolymer of ethylene glycol with propylene glycol; a glycerol ester; a polyethyleneimine derivative; a polyvinyl alcohol derivative; a polyacrylic acid derivative; a polyacrylamide derivative; a dextran derivative; a polyglycerol derivative; a chitosan derivative; a polyvinylpyrrolidone derivative; a polyaspartic amide derivative; a poly-L-lysine derivative; a mannan derivative; and a pullulan derivative.

Examples of the lipid used for the lipid membrane in the present invention are phospholipid, glyceroglycolipid, sphingoglycolipid, cholesterol and synthetic lipid, and phospholipid is particularly preferably used. With regard to the phospholipid, glyceroglycolipid and sphingoglycolipid, the same ones as mentioned above may be exemplified and, with regard to the synthetic lipid, there may be exemplified fluorine-added phosphatidylcholine, fluorine-added detergent and dialkylammonium bromide.

With regard to the method for the preparation of an aqueous solution containing a polar organic solvent in which the fine particles are dispersed and the lipid-is dissolved to be used in the present invention, there may be exemplified a method where fine particles are dispersed in an aqueous solution containing a polar organic solvent (liquid A), lipid is dissolved in a polar organic solvent or an aqueous solution containing a polar organic solvent which is the same as or different from the said aqueous solution containing a polar organic solvent (liquid B) and then the liquid A and the liquid B are mixed.

With regard to the method for coating the fine particles with lipid membrane according to the present invention, the following method may be specifically exemplified.

(step 1) The fine particles are dispersed (suspended) in an aqueous solution containing a polar organic solvent, preferably in an aqueous solution containing an alcohol such as ethanol;

(step 2) The lipid which is dissolved in an aqueous solution containing a polar organic solvent which is the same as or different from the aqueous solution containing the said polar organic solvent or, preferably in the same aqueous solution containing the polar organic solvent or in the polar organic solvent is added to the suspension prepared in the step 1, followed by mixing. At that time, a water-soluble polymer derivative may be further added thereto and there is no particular limitation for the amount of the water-soluble polymer derivative to be added here; and (step 3) Small amounts of water are added to the mixed solution prepared in the step 2, dialysis is carried out or the polar organic solvent is evaporated so as to decrease the rate of the polar organic solvent in the mixed solution whereby the dissolved lipid (lipid and the water-soluble polymer derivative, in case the water-soluble polymer derivative is added in the step 2) is accumulated on the surface of the fine particles, a lipid membrane is formed on the surface of the fine particles and closed vesicles in which the fine particles are enclosed are prepared.

There is no particular limitation for the rate of the polar organic solvent in the aqueous solution containing the polar organic solvent used in the method of the present invention so far as the conditions that the fine particles are present without being dissolved, and that the components constituting the lipid membrane coating the fine particles are dissolved is satisfied and, although the rate varies depending upon the solvent and the fine particles used and the type of the lipid used, it is preferably 30% or more and, more preferably, it is 60 to 90%. Further, with regard to the rate of the polar organic solvent in the mixed solution after decreased during the above-mentioned step 3, there is no particular limitation so far as the rate is within such an extent that the dissolved lipid (lipid and the water-soluble polymer derivative, in case the water-soluble polymer derivative is added in the step 2) is/are accumulated on the surface of the fine particles whereby a lipid membrane can be formed on the surface of the fine particles and, preferably, concentration of the polar organic solvent in the aqueous solution is 50% or less.

Although the rate of the fine particles used in the present invention to the aqueous solution containing the polar organic solvent or to the preparation obtained by the method of the present invention is not particularly limited so far as the said fine particles can be coated with the lipid membrane, it is preferably 1 µg/mL to 1 g/mL or, more preferably, 0.1 to 500 mg/mL.

Although the rate of the lipid used in the present invention to the aqueous solution containing the polar organic solvent or to the preparation obtained by the method of the present invention is not particularly limited so far as the fine particles can be coated therewith, it is preferably 1 µg/mL to 1 g/mL or, more preferably, 0.1 to 400 mg/mL.

Independently of the type of the fine particles used, it is basically possible to coat the fine particles with the lipid membrane by the same method as mentioned above.

With regard to the polar organic solvent and the lipid used in the present invention, commercially available ones may be used.

The fine particles used in the present invention are available from the market or may be manufactured by known methods.

For example, for the manufacture of liposome constituting the fine particles, a known method for the preparation of liposome may be applied. With regard to a known method for the preparation of liposome, there may be exemplified a liposome preparation method by Bangham, et al. [J. Mol. Biol., 13, 238 (1965)], an ethanol injection method [J. Cell. Biol., 66, 621 (1975)], a French press method [FEBS Lett., 99, 210 (1979)], a freeze-thaw method [Arch. Biochem. Biophys., 212, 186 (1981)], a reverse phase evaporation method [Proc. Natl. Acad. Sci. USA, 75, 4194 (1978)] and a pH gradient method (Japanese Patent No. 2,572,554; Japanese Patent No. 2,659,136; etc.).

Improvement in quality of liposome surface by nonionic detergent, cationic detergent, anionic detergent, polysaccharide or a derivative thereof, a polyoxyethylene derivative, etc. may also be carried out optionally, and those liposomes where quality of the surface is improved may also be used as fine particles of the present invention [Stealth Liposomes, ed. by D. D. Lasic and F. Martin, CRC Press Inc., Florida, 93-102 (1995)].

With regard to a solution for suspending the liposome in the manufacture of liposome constituting the fine particles, there may be used acid, alkali, various kinds of buffers, physiological saline, amino acid infusion solution, etc. in addition to water. It is also possible to add an antioxidant such as citric acid, ascorbic acid, cysteine and ethylenediamine tetraacetic acid (EDTA) to a liposome suspension. It is further possible to add glycerol, glucose, sodium chloride, etc. as an isotonizing solution.

It is also possible that a drug and lipid are dissolved in an organic solvent such as ethanol, that the solvent is evaporated therefrom, a physiological saline or the like is added to the residue and that the mixture is shaken and stirred to form liposome.

A water-soluble polymer derivative may be added when the drug is enclosed in liposome, when a complex of the liposome with the drug is formed or after that.

There is no particular limitation for an average particle size of the liposome and it may be freely selected upon demand. Examples of a method for adjusting the average particle size are an extrusion method and a method where a big multilamellar liposome (MLV) is mechanically pulverized using Manton-gaulin, microfluidizers, etc. [R. H. Muller, S. Benita, B. Bohm (ed.), "Emulsion and Nanosuspensions for the Formulation of Poorly Soluble Drugs", High-Pressure Homogenization Techniques for the Production of Liposome Dispersions: Potential and Limitations, M. Brandl, 267-294 (1998) (Scientific Publishers, Stuttgart, Germany)].

A method for the formation of a complex combined by two or more members selected from a drug constituting the fine particles, lipid assembly, liposome, fine particles in emulsion, natural polymer, synthetic polymer, metal colloid, cationic lipid, anionic lipid, a fine particle preparation and a water-soluble polymer derivative may be a method where the drug is just mixed with lipid, polymer, etc. in water and, at that time, particle size selecting step, aseptic step, etc. may be further added if necessary. It is also possible that formation of the complex is carried out in various solvents such as acetone and ether.

With regard to the fine particles used in the present invention and/or the lipid membrane which coats the fine particles obtained by the present invention, it is possible that the surface thereof is modified by a protein such as an antibody, a saccharide, glycolipid, an amino acid, a nucleic acid and various low-molecular compounds and polymer compounds, or that such a substance is just added to the fine particles and/or lipid membrane followed by using.

For example, in order to apply to targeting, it is possible that the coated membrane is further subjected to a surface modification of the lipid membrane using a protein (including an antibody), a peptide, a fatty acid, etc. [Stealth Liposomes, ed. by D. D. Lasic and F. Martin, CRC Press Inc., Florida, 93-102, (1995)].

The fine particles coated with the lipid membrane obtained by the method of the present invention may be used as they are, or depending upon the purpose of use, storage condition, etc., they may be freeze-dried after addition of excipient such as mannitol, lactose, trehalose, maltose or glycine thereto. Freeze preservation after addition of a freeze-preserving agent such as glycerol is also possible. It is further possible that granulation, drying, etc. are carried out together with an appropriate excipient to manufacture an oral preparation such as capsules, tablets or granules.

The fine particles coated with the lipid membrane obtained by the method of the present invention may be suspended using acid, alkali, various buffers, physiological saline, amino acid transfusion solution, etc. in addition to water. It is also possible that an antioxidant such as citric acid, ascorbic acid, cysteine or EDTA is added to a liposome suspension. It is further possible to add glycerol, glucose, sodium chloride or the like as an isotonizing agent.

The preparation obtained by the method of the present invention is generally used as injections but it is also possible to use after preparing into oral preparations, nasal drops, ophthalmic solutions, percutaneous preparations, suppositories, inhalation preparations or the like.

The preparation obtained by the present invention may be used with such an object as stabilization of the drug in living body components such as blood components or in blood or gastrointestinal tracts, reduction of side effect, increase in accumulation property to target organ such as tumor, improvement in absorption per os or via mucous membrane, etc.

Examples and Comparative Examples of the present invention will be shown hereunder.

BEST MODE FOR CARRYING OUT THE INVENTION

EXAMPLE 1

Distilled water (3 mL) was added to 10 mg of dextran fluorescein anionic (FD) (manufactured by Molecular Probes), 60 mg of DOTAP (manufactured by Avanti) and 24 mg of PEG-DSPE (manufactured by Avanti), followed by shaking and stirring in a vortex mixer. The suspension was passed, at room temperature, through a polycarbonate membrane filter of 0.4 μm for 20 times and then a polycarbonate membrane filter of 0.1 μm for 20 times and 4 mL of ethanol was added thereto. After that, to this suspension was added a solution prepared by dissolving 240 mg of egg yolk phosphatidylcholine (EggPC) and 50 mg of PEG-DSPE in 1 mL of ethanol. Distilled water (92 mL) was gradually added to the suspension so that the concentration of ethanol was adjusted to 5% or lower. The resulting liposome suspension was subjected to an ultracentrifugal separation (110,000×g at 25° C. for 1 hour) and the supernatant liquid was removed. A phosphate-buffered saline (PBS) was added thereto followed by subjecting to re-suspending so as to adjust the total lipid concentration to 30 mg/mL, whereupon a liposome suspension (Preparation 1) was obtained.

When an average particle size of the liposome was measured by means of a dynamic light scattering (DLS) [A model ELS-800, Otsuka Electronics, Ltd.; hereinafter the same one was used], it was found to be 134 nm.

EXAMPLE 2

Distilled water (3 mL) was added to 10 mg of FD, 60 mg of DOTAP and 24 mg of PEG-DSPE, followed by shaking and stirring in a vortex mixer. The suspension was passed, at room temperature, through a polycarbonate membrane filter of 0.4 μm for 20 times and then a polycarbonate membrane filter of 0.1 μm for 20 times and 4 mL of ethanol was added thereto. After that, to this suspension was added a solution prepared by dissolving 120 mg of EggPC and 25 mg of PEG-DSPE in 1 mL of ethanol. Distilled water (92 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 2) was obtained.

When an average particle size of the liposome was measured by means of DLS, it was found to be 179 nm.

EXAMPLE 3

Distilled water (3 mL) was added to 10 mg of FD, 60 mg of DOTAP and 24 mg of PEG-DSPE, followed by shaking and stirring in a vortex mixer. The suspension was passed, at room temperature, through a polycarbonate membrane filter of 0.4 μm for 20 times and then a polycarbonate membrane filter of 0.1 μm for 20 times and 4 mL of ethanol was added thereto. After that, to this suspension was added a solution prepared by dissolving 60 mg of EggPC and 12.5 mg of PEG-DSPE in 1 mL of ethanol. Distilled water (92 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 3) was obtained.

When an average particle size of the liposome was measured by means of DLS, it was found to be 184 nm.

EXAMPLE 4

Distilled water (3 mL) was added to 10 mg of FD and 60 mg of DOTAP, followed by shaking and stirring in a vortex mixer. The suspension was passed, at room temperature, through a polycarbonate membrane filter of 0.4 μm for 20 times and then a polycarbonate membrane filter of 0.1 μm for 20 times and 4 mL of ethanol was added thereto. After that, to this suspension was added a solution prepared by dissolving 240 mg of EggPC and 74 mg of PEG-DSPE in 1 mL of ethanol. Distilled water (92 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 4) was obtained.

When an average particle size of the liposome was measured by means of DLS, it was found to be 131 nm.

EXAMPLE 5

Distilled water (3 mL) was added to 10 mg of FD and 60 mg of DOTAP, followed by shaking and stirring in a vortex mixer. The suspension was passed, at room temperature, through a polycarbonate membrane filter of 0.4 μm for 20 times and then a polycarbonate membrane filter of 0.1 μm for 20 times and 4 mL of ethanol was added thereto. After that, to this suspension was added a solution prepared by dissolving 240 mg of EggPC in 1 mL of ethanol. Distilled water (92 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 5) was obtained.

When an average particle size of the liposome was measured by means of DLS, it was found to be 458 nm.

EXAMPLE 6

Distilled water (1.49 mL) and 0.01 mL of an aqueous solution of sodium hydroxide (1 mol/L) were added to 2.5 mg of fluorescein isothiocyanate (FITC)-labeled insulin (F-Ins), 30 mg of DOTAP and 12 mg of PEG-DSPE, followed by shaking and stirring in a vortex mixer. The suspension was passed, at room temperature, through a polycarbonate membrane filter of 0.4 μm for 20 times and then a polycarbonate membrane filter of 0.1 μm for 20 times and 2 mL of ethanol was added thereto. After that, to this suspension was added a solution prepared by dissolving 120 mg of EggPC and 25 mg of PEG-DSPE in 0.5 mL of ethanol. Distilled water (46 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 6) was obtained.

When an average particle size of the liposome was measured by means of DLS, it was found to be 132 nm.

EXAMPLE 7

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.5 mL) was added 0.25 mL of a solution prepared by dissolving fluorescein isothiocyanate-bound phosphorothioate (F-PS) (manufactured by Sci Media) in distilled water to adjust to 15 mg/mL, followed by adding 1 mL of ethanol thereto. To this suspension was further added 0.25 mL of a solution of EggPC/PEG-DSPE/ethanol (120 mg/25 mg/mL). Distilled water (23 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension was obtained. PEG-DSPE (ratio of PEG-DSPE to EggPC is 50:120 (weight:weight)) was dissolved in a small amount of ethanol (4% by volume of the liposome suspension) followed by mixing with the liposome suspension and heating at 70° C. for 2 minutes. PBS was added thereto so as to adjust the total lipid concentration to 30 mg/mL, whereupon a liposome suspension (Preparation 7) was obtained.

When an average particle size of the liposome was measured by means of DLS, it was found to be 111 nm.

EXAMPLE 8

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.4 mL) was added 0.2 mL of a solution prepared by dissolving F-PS in distilled water to adjust to 10 mg/mL followed by adding 0.8 mL of ethanol thereto. To this suspension was further added 0.2 mL of a solution of EggPC/PEG-DSPE/ethanol (240 mg/50 mg/mL). Distilled water (18.4 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 8) was obtained.

When an average particle size of the liposome was measured by means of DLS, it was found to be 112 nm.

EXAMPLE 9

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.4 mL) was added 0.2 mL of a solution prepared by dissolving F-PS in distilled water to adjust to 15 mg/mL followed by adding 0.8 mL of ethanol thereto. To this suspension was further added 0.2 mL of a solution of EggPC/PEG-DSPE/ethanol (240 mg/50 mg/mL). Distilled water (18.4 mL) was gradually added to this suspension so that concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 9) was obtained.

When an average particle size of the liposome was measured by means of DLS, it was found to be 137 nm.

EXAMPLE 10

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.4 mL) was added 0.2 mL of a solution prepared by dissolving F-PS in distilled water to adjust to 17.5 mg/mL followed by adding 0.8 mL of ethanol thereto. To this suspension was further added 0.2 mL of a solution of EggPC/PEG-DSPE/ethanol (240 mg/50 mg/mL). Distilled water (18.4 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 10) was obtained.

When an average particle size of the liposome was measured by means of DLS, it was found to be 132 nm.

EXAMPLE 11

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.4 mL) was added 0.2 mL of a solution prepared by dissolving F-PS in distilled water to adjust to 20 mg/mL followed by adding 0.8 mL of ethanol thereto. To this suspension was further added 0.2 mL of a solution of EggPC/PEG-DSPE/ethanol (240 mg/50 mg/mL). Distilled water (18.4 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 11) was obtained.

When an average particle size of the liposome was measured by means of DLS, it was found to be 164 nm.

EXAMPLE 12

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.25 mL) was added 0.125 mL of a solution prepared by dissolving F-PS in distilled water to adjust to 15 mg/mL followed by adding 0.5 mL of ethanol thereto. To this suspension was further added 0.125 mL of a solution of EggPC/PEG-DSPE/ethanol (240 mg/100 mg/mL). Distilled water (11.5 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 12) was obtained.

When an average particle size of the liposome was measured by means of DLS, it was found to be 122 nm.

EXAMPLE 13

Mixing was carried out to prepare DOTAP/PEG-DSPE/distilled water (30 mg/12 mg/mL), followed by shaking and stirring in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times. To this suspension (0.25 mL) was added 0.125 mL of a solution prepared by dissolving F-PS in distilled water to adjust to 15 mg/mL followed by adding 0.5 mL of ethanol thereto. To this suspension was further added 0.125 mL of a solution of EggPC/PEG-DSPE/ethanol (360 mg/150 mg/mL). Distilled water (11.5 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS was added thereto followed by subjecting to re-suspending so as to adjust the total lipid concentration to 30 mg/mL, whereupon a liposome suspension (Preparation 13) was obtained.

When an average particle size of the liposome was measured by means of DLS, it was found to be 165 nm.

EXAMPLE 14

DOTAP (30 mg/mL) and PEG-DSPE (12 mg/mL) suspensions were shaken and stirred in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times to give a suspension of liposome where particle size was around 80 nm. Under stirring by a stirrer, 125 µL of a 15 mg/mL aqueous solution of F-PS was added to 250 µL of the suspension followed by adding 0.5 mL of ethanol thereto. To this suspension was further added 125 µL of a solution where 120 mg of EggPC and 25 mg of polyoxyethylene hydrogenated castor oil 60 (manufactured by NOF CORPORATION) were dissolved in 1 mL of ethanol. Distilled water (11.5 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS (40 µL) was added thereto followed by subjecting to re-suspending and further diluting with PBS, whereupon a liposome suspension of 3 mg/mL of F-PS was obtained. PEG-DSPE (ratio of PEG-DSPE to EggPC is 50:120 (weight:weight)) was dissolved in a small amount (about ⅕ by volume of the liposome suspension) of ethanol. Each of the liposome suspension and the ethanolic solution of PEG-DSPE was heated at 70° C. for 2 minutes. Then the liposome suspension was added to the ethanolic solution of PEG-DSPE and, after mixing, the mixture was heated at 70° C. for 2 minutes and cooled with water. To the resulting liposome suspension was added PBS to dilute so that the total lipid concentration was adjusted to 30 mg/mL, whereupon a liposome suspension (Preparation 14) was obtained.

When an average particle size of the liposome was measured by means of DLS, it was found to be 116 nm.

EXAMPLE 15

DOTAP (30 mg/mL) and PEG-DSPE (12 mg/mL) suspensions were shaken and stirred in a vortex mixer. The suspension was passed, at room temperature, through a polycarbonate membrane filter of 0.4 µm for 20 times, a polycarbonate membrane filter of 0.1 µm for 20 times and additionally a polycarbonate membrane filter of 0.05 µm for 20 times to give a suspension of liposome where particle size was around 80 nm. Under stirring by a stirrer, 250 µL of a 15 mg/mL aqueous solution of F-PS was added to 500 of the suspension followed by adding 1 mL of ethanol thereto. To this suspension was further added 250 µL of a solution where 120 mg of EggPC and 25 mg of Cremophor EL (manufactured by Sigma) were dissolved in 1 mL of ethanol. Distilled water (23 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS (40 µL) was added thereto followed by subjecting to re-suspending and further diluting with PBS, whereupon a liposome suspension of 3 mg/mL of F-PS was obtained. PEG-DSPE (ratio of PEG-DSPE to EggPC is 50:120 (weight:weight)) was dissolved in a small amount (about ⅕ by volume of the liposome suspension) of ethanol. Each of the liposome suspension and the ethanolic solution of PEG-DSPE was heated at 70° C. for 2 minutes. Then the liposome suspension was added to the ethanolic solution of PEG-DSPE and, after mixing, the mixture was heated at 70° C. for 2 minutes and cooled with water. To the resulting liposome suspension was added PBS to dilute so that the total lipid concentration was adjusted to 30 mg/mL, whereupon a liposome suspension (Preparation 15) was obtained.

When an average particle size of the liposome was measured by means of DLS, it was found to be 140 nm.

EXAMPLE 16

DOTAP (30 mg/mL) and PEG-DSPE (12 mg/mL) suspensions were shaken and stirred in a vortex mixer. The suspension was passed, at room temperature, through a polycarbonate membrane filter of 0.4 μm for 20 times, a polycarbonate membrane filter of 0.1 μm for 20 times and additionally a polycarbonate membrane filter of 0.05 μm for 20 times to give a suspension of liposome where particle size was around 80 nm. Under stirring by a stirrer, 120 μL of a 15 mg/mL aqueous solution of F-PS was added to 250 μL of the suspension followed by adding 0.5 mL of ethanol thereto. To this suspension was further added 125 μL of a solution where 25 mg of Tween 80 was dissolved in 1 mL of an ethanolic solution of 120 mg/mL EggPC. Distilled water (11.5 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS (40 μL) was added thereto followed by subjecting to re-suspending and further diluting with PBS, whereupon a liposome suspension of 3 mg/mL of F-PS was obtained. PEG-DSPE (ratio of PEG-DSPE to EggPC is 50:12.0 (weight:weight)) was dissolved in a small amount (about ⅕ by volume of the liposome suspension) of ethanol. Each of the liposome suspension and the ethanolic solution of PEG-DSPE was heated at 70° C. for 2 minutes. Then the liposome suspension was added to the ethanolic solution of PEG-DSPE and, after mixing, the mixture was heated at 70° C. for 2 minutes and cooled with water. To the resulting liposome suspension was added PBS to dilute so that the total lipid concentration was adjusted to 30 mg/mL, whereupon a liposome suspension (Preparation 16) was obtained.

When an average particle size of the liposome was measured by means of DLS, it was found to be 151 nm.

EXAMPLE 17

DOTAP (30 mg/mL) and PEG-DSPE (12 mg/mL) suspensions were shaken and stirred in a vortex mixer. The suspension was passed, at room temperature, through a polycarbonate membrane filter of 0.4 μm for 20 times, a polycarbonate membrane filter of 0.1 μm for 20 times and additionally a polycarbonate membrane filter of 0.05 μm for 20 times to give a suspension of liposome where particle size was around 80 nm. Under stirring by a stirrer, 125 μL of a 15 mg/mL aqueous solution of F-PS was added to 250 μL of the suspension followed by adding 0.5 mL of ethanol thereto. To this suspension was further added 125 μL of a solution where 120 mg of EggPC, 120 mg of Span 20 (manufactured by Kanto Kagaku) and 50 mg of PEG-DSPE were dissolved in 2 mL of ethanol. Distilled water (11.5 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS (40 μL) was added thereto followed by subjecting to re-suspending and further diluting with PBS, whereupon a liposome suspension of 3 mg/mL of F-PS was obtained. PEG-DSPE (ratio of PEG-DSPE to EggPC is 50:120 (weight:weight)) was dissolved in a small amount (about ⅕ by volume of the liposome suspension) of ethanol. Each of the liposome suspension and the ethanolic solution of PEG-DSPE was heated at 70° C. for 2 minutes. Then the liposome suspension was added to the ethanolic solution of PEG-DSPE and, after mixing, the mixture was heated at 70° C. for 2 minutes and cooled with water. To the resulting liposome suspension was added PBS to dilute so that the total lipid concentration was adjusted to 30 mg/mL, whereupon a liposome suspension (Preparation 17) was obtained.

When an average particle size of the liposome was measured by means of DLS, it was found to be 131 nm.

EXAMPLE 18

DOTAP (30 mg/mL) and PEG-DSPE (12 mg/mL) suspensions were shaken and stirred in a vortex mixer. The suspension was passed, at room temperature, through a polycarbonate membrane filter of 0.4 μm for 20 times, a polycarbonate membrane filter of 0.1 μm for 20 times and additionally a polycarbonate membrane filter of 0.05 μm for 20 times to give a suspension of liposome where particle size was around 80 nm. Under stirring by a stirrer, 250 μL of a 15 mg/mL aqueous solution of F-PS was added to 500 μL of the suspension followed by adding 1 mL of ethanol thereto. To this suspension was further added 250 μL of a solution where 120 mg of EggPC and 12.5 mg of Cremophor EL (manufactured by Sigma) were dissolved in 1 mL of ethanol. Distilled water (23 mL) was gradually added to this suspension so that the concentration of ethanol was adjusted to 5% or lower. The resulting liposome suspension was subjected to an ultracentrifugal separation (110,000×g at 25° C. for 1 hour) and the supernatant liquid was removed. PBS (40 μL) was added thereto followed by subjecting to re-suspending and further diluting with PBS, whereupon a liposome suspension of 3 mg/mL of F-PS was obtained. PEG-DSPE (ratio of PEG-DSPE to EggPC is 50:120 (weight:weight)) was dissolved in a small amount (about ⅕ by volume of the liposome suspension) of ethanol. Each of the liposome suspension and the ethanolic solution of PEG-DSPE was heated at 70° C. for 2 minutes. Then the liposome suspension was added to the ethanolic solution of PEG-DSPE and, after mixing, the mixture was heated at 70° C. for 2 minutes and cooled with water. To the resulting liposome suspension was added PBS to dilute so as to adjust the total lipid concentration to 30 mg/mL, whereupon a liposome suspension (Preparation 18) was obtained.

When an average particle size of the liposome was measured by means of DLS, it was found to be 133 nm.

EXAMPLE 19

To 589 mg of egg yolk lecithin (manufactured by QP CORPORATION) was added 11.8 mL of a 50 mmol/L aqueous solution of potassium dihydrogen phosphate, followed by shaking and stirring in a vortex mixer. The suspension was passed, at room temperature, through a polycarbonate membrane filter of 0.1 μm for 30 times. The suspension (40 μL) was mixed with a mixed solution comprising 1 mL of an aqueous solution of 1 mg/mL of G-CSF (manufactured by Kyowa Hakko; Nartograstim; genetically recombined human G-CSF mutant) and 1 mL of an aqueous solution of 2 mg/mL of sodium dextransulfate (manufactured by Merck), and pH value of the mixed solution was adjusted to 4 using aqueous solutions of hydrochloric acid of 1 mol/L and 0.1 mol/L (manufactured by Kanto Kagaku). To 500 μL of this mixed solution were added 753 μL of ethanol and then 80 μL of an ethanolic solution of 50 mg/mL of egg yolk lecithin. Distilled water (7 mL) was gradually added to this suspension so that the concentration of ethanol was adjusted to 10% or lower. The resulting liposome suspension was subjected to an ultracentrifugal separation (146,000×g at 25° C. for 1 hour) and the supernatant liquid was removed. Water was added thereto followed by subjecting to re-suspending so as to make the total amount 500 µL, whereupon a liposome suspension (Preparation 19) was obtained.

When an average particle size of the liposome was measured by means of DLS, it was found to be 316 nm.

EXAMPLE 20

To 588 mg of egg yolk lecithin and 205 mg of PEG-DSPE was added an appropriate amount of ethanol at room temperature to dissolve them and then ethanol was evaporated, followed by drying in vacuo. 11.8 mL of a 50 mmol/L aqueous solution of potassium dihydrogen phosphate was added thereto followed by shaking and stirring in a vortex mixer. The suspension was passed, at room temperature, through a polycarbonate membrane filter of 0.1 µm for 30 times. The suspension (40 µL) was mixed with a mixed solution comprising 1 mL of an aqueous solution of 1 mg/mL of G-CSF and 1 mL of an aqueous solution of 2 mg/mL of sodium dextransulfate, and pH value of the mixed solution was adjusted to 4 using aqueous solutions of hydrochloric acid of 1 mol/L and 0.1 mol/L. To 500 µL of this mixed solution was added 753 µL of ethanol, and then 80 µL of ethanol containing 50 mg/mL of egg yolk lecithin and 16.7 mg/mL of PEG-DSPE was added thereto. Distilled water (7 mL) was gradually added to this suspension so that the concentration of ethanol was adjusted to 10% or lower. The resulting liposome suspension was subjected to an ultracentrifugal separation (146,000×g at 25° C. for 1 hour) and the supernatant liquid was removed. Water was added thereto followed by subjecting to re-suspending so as to make the total amount 500 µL, whereupon a liposome suspension (Preparation 20) was obtained.

When an average particle size of the liposome was measured by means of DLS, it was found to be 316 nm.

EXAMPLE 21

To 598 mg of egg yolk lecithin and 68.8 mg of sucrose fatty acid ester (manufactured by Mitsubishi Chemical) was added an appropriate amount of ethanol at room temperature to dissolve them and then ethanol was evaporated, followed by drying in vacuo. 12.0 mL of a 50 mmol/L aqueous solution of potassium dihydrogen phosphate was added thereto followed by shaking and stirring in a vortex mixer. The suspension was passed, at room temperature, through a polycarbonate membrane filter of 0.1 µm for 30 times. The suspension (40 µL) was mixed with a mixed solution comprising 1 mL of an aqueous solution of 1 mg/mL of G-CSF and 1 mL of an aqueous solution of 2 mg/mL of sodium dextransulfate, and pH value of the mixed solution was adjusted to 4 with aqueous solutions of hydrochloric acid of 1 mol/L and 0.1 mol/L. To 500 µL of this mixed solution was added 753 µL of ethanol, and then 80 µL of ethanol where 50 mg/mL of egg yolk lecithin and 4.5 mg/mL of sucrose fatty acid ester were dissolved therein was added thereto. Distilled water (7 mL) was gradually added to this suspension so that the concentration of ethanol was adjusted to 10% or lower. The resulting liposome suspension was subjected to an ultracentrifugal separation (146,000×g at 25° C. for 1 hour) and the supernatant liquid was removed. Water was added thereto followed by subjecting to re-suspending so as to make the total amount 500 µL, whereupon a liposome suspension (Preparation 21) was obtained.

When an average particle size of the liposome was measured by means of DLS, it was found to be 242 nm.

EXAMPLE 22

To 150 mg of egg yolk lecithin and 60 mg of PEG-DSPE was added 5 mL of distilled water, followed by shaking and stirring in a vortex mixer. The suspension was passed, at room temperature, through a polycarbonate membrane filter of 0.08 µm for 20 times. The suspension (571 µL) was mixed with a mixed solution comprising 119 µL of an aqueous solution of potassium dihydrogen phosphate containing 1.4 mg/mL of G-CSF and 167 µL of an aqueous solution of 2 mg/mL of sodium dextransulfate, and pH value of the mixed solution was adjusted to 4 with aqueous solutions of hydrochloric acid of 1 mol/L and 0.1 mol/L. To 0.5 mL of this mixed solution was added 666 µL of ethanol, and then 167 µL of a solution where 120 mg of egg yolk phosphatidylcholine (EggPC; manufactured by NOF CORPORATION) and 25 mg of PEG-DSPE were dissolved in 1 mL of ethanol was added thereto. Distilled water (47 mL) was gradually added to this suspension so that the concentration of ethanol was adjusted to 5% or lower. The resulting liposome suspension was subjected to an ultracentrifugal separation (146,000×g at 4° C. for 1 hour) and the supernatant liquid was removed. Distilled water was added thereto followed by subjecting to re-suspending, whereupon a liposome suspension (Preparation 22) was obtained.

When an average particle size of the liposome was measured by means of DLS, it was found to be 126 nm.

EXAMPLE 23

To 150 mg of egg yolk lecithin and 60 mg of PEG-DSPE was added 5 mL of distilled water followed by shaking and stirring in a vortex mixer. The suspension was passed, at room temperature, through a polycarbonate membrane filter of 0.08 µm for 20 times and then a polycarbonate membrane filter of 0.03 µm for 7 times. The suspension (286 µL) was mixed with 286 µL of a mixed solution comprising 119 µL of an aqueous solution of potassium dihydrogen phosphate containing 1.4 mg/mL of G-CSF and 167 µL of an aqueous solution of 2 mg/mL of sodium dextransulfate, and pH value of the mixed solution was adjusted to 4 with aqueous solutions of hydrochloric acid of 1 mol/L and 0.1 mol/L. To 0.25 mL of this mixed solution was added 333 µL of ethanol, and then 84 µL of a solution where 120 mg of egg yolk phosphatidylcholine and 25 mg of PEG-DSPE were dissolved in 1 mL of ethanol was added thereto. Distilled water (23.5 mL) was gradually added to this suspension so that the concentration of ethanol was adjusted to 5% or lower. The resulting liposome suspension was subjected to an ultracentrifugal separation (146,000×g at 4° C. for 1 hour) and the supernatant liquid was removed. Re-suspending was carried out by adding an aqueous solution of potassium dihydrogen phosphate, whereupon a liposome suspension (Preparation 23) was obtained.

When an average particle size of the liposome was measured by means of DLS, it was found to be 146 nm.

EXAMPLE 24

To 150 mg of egg yolk lecithin and 60 mg of PEG-DSPE was added 5 mL of distilled water followed by shaking and stirring in a vortex mixer. The suspension was passed, at room temperature, through a polycarbonate membrane filter of 0.08 μm for 20 times and then a polycarbonate membrane filter of 0.05 μm for 20 times. The suspension (428 μL) was mixed with a mixed solution comprising 89 μL of an aqueous solution of potassium dihydrogen phosphate containing 1.4 mg/mL of G-CSF and 125 μL of an aqueous solution of 2 mg/mL of sodium dextransulfate, and pH value of the mixed solution was adjusted to 4 with aqueous solutions of hydrochloric acid of 1 mol/L and 0.1 mol/L. To 0.5 mL of this mixed solution was added 666 μL of ethanol, and then 167 μL of a solution where 120 mg of egg yolk phosphatidylcholine and 25 mg of PEG-DSPE were dissolved in 1 mL of ethanol was added thereto. Distilled water (47 mL) was gradually added to this suspension so that the concentration of ethanol was adjusted to 5% or lower. The resulting liposome suspension was subjected to an ultracentrifugal separation (146,000×g at 4° C. for 1 hour) and the supernatant liquid was removed. Re-suspending was carried out by adding an aqueous solution of potassium dihydrogen phosphate, whereupon a liposome suspension (Preparation 24) was obtained.

When an average particle size of the liposome was measured by means of DLS, it was found to be 134 nm.

EXAMPLE 25

To 150 mg of egg yolk lecithin and 60 mg of PEG-DSPE was added 5 mL of distilled water, followed by shaking and stirring in a vortex mixer. The suspension was passed, at room temperature, through a polycarbonate membrane filter of 0.08 μm for 20 times and then a polycarbonate membrane filter of 0.05 μm for 20 times. The suspension (500 μL) was mixed with a mixed solution comprising 20 μL of a PBS solution containing 1,000,000 units/mL of interferon α-2b (manufactured by Research Diagnostics), 150 μL of an aqueous solution of 2 mg/mL of sodium dextransulfate and 80 μL of distilled water, and pH value of the mixed solution was adjusted to 4 with aqueous solutions of hydrochloric acid of 1 mol/L and 0.1 mol/L. To 0.5 mL of this mixed solution was added 666 μL of ethanol, and then 167 μL of a solution where 120 mg of egg yolk phosphatidylcholine and 25 mg of PEG-DSPE were dissolved in 1 mL of ethanol was added thereto. Distilled water (47 mL) was gradually added to this suspension so that the concentration of ethanol was adjusted to 5% or lower. The resulting liposome suspension was subjected to an ultracentrifugal separation (146,000×g at 4° C. for 1 hour) and the supernatant liquid was removed. Re-suspending was carried out by adding an aqueous solution of potassium dihydrogen phosphate, whereupon a liposome suspension (Preparation 25) was obtained.

When an average particle size of the liposome was measured by means of DLS, it was found to be 164 nm.

COMPARATIVE EXAMPLE 1

EggPC (215 mg), 61 mg of DOTAP and 54 mg of cholesterol (Chol) were dissolved in chloroform and the solvent was evaporated therefrom in vacuo. To the resulting thin layer was added 5 mL of an aqueous solution of FD (2 mg/mL). The suspension was passed, at room temperature, through a polycarbonate membrane filter of 0.4 μm for 20 times and then a polycarbonate membrane filter of 0.1 μm for 20 times. PBS was added thereto so as to adjust the total lipid concentration to 30 mg/mL, whereupon a liposome suspension (Preparation a) was obtained.

When an average particle size of the liposome was measured by means of DLS, it was found to be 134 nm.

COMPARATIVE EXAMPLE 2

EggPC (215 mg), 61 mg of DOTAP and 54 mg of Chol were dissolved in chloroform and the solvent was evaporated therefrom in vacuo. To the resulting thin layer was added 5 mL of an aqueous solution of FD (2 mg/mL). The suspension was passed, at room temperature, through a polycarbonate membrane filter of 0.4 μm for 20 times and then a polycarbonate membrane filter of 0.1 μm for 20 times. An ethanolic solution of PEG-DSPE with a concentration of 1471 mg/mL (0.05 mL) was added thereto followed by heating at 70° C. for 5 minutes, whereupon the surface of the liposome was coated with PEG. PBS was added thereto so as to adjust the total lipid concentration to 30 mg/mL, whereupon a liposome suspension (Preparation b) was obtained.

When an average particle size of the liposome was measured by means of DLS, it was found to be 143 nm.

COMPARATIVE EXAMPLE 3

Hydrogenated soybean phosphatidylcholine (HSPC) (300 mg), 100 mg of Chol and 100 mg of PEG-DSPE were dissolved in chloroform and the solvent was evaporated therefrom in vacuo. To the resulting thin layer was added 8 mL of an aqueous solution of FD (18.8 mg/mL). The suspension was passed, at 70C.°, through a polycarbonate membrane filter of 0.4 μm for 4 times and then a polycarbonate membrane filter of 0.1 μm for 10 times. The resulting liposome suspension was subjected to a ultracentrifugal separation (110,000×g at 25° C. for 1 hour) and the supernatant liquid was removed. Re-suspending was carried out by adding thereto PBS so as to adjust the total lipid concentration to 30 mg/mL, whereupon a liposome suspension (Preparation c) was obtained.

When an average particle size of the liposome was measured by means of DLS, it was found to be 149 nm.

COMPARATIVE EXAMPLE 4

EggPC (215 mg), 61 mg of DOTAP and 54 mg of Chol were dissolved in chloroform and the solvent was evaporated therefrom in vacuo. To the resulting thin layer were added 5 mL of an aqueous solution of FD (2 mg/mL). The suspension was passed, at room temperature, through a polycarbonate membrane filter of 0.4 μm for 20 times and then a polycarbonate membrane filter of 0.1 μm for 20 times. The resulting liposome suspension was subjected to a ultracentrifugal separation (110,000×g at 25° C. for 1 hour) and the supernatant liquid was removed. Re-suspending was carried out by adding thereto PBS so as to adjust the total lipid concentration to 30 mg/mL, whereupon a liposome suspension (Preparation d) was obtained.

When an average particle size of the liposome was measured by means of DLS, it was found to be 141 nm.

COMPARATIVE EXAMPLE 5

EggPC (215 mg), 61 mg of DOTAP and 54 mg of Chol were dissolved in chloroform and the solvent was evaporated therefrom in vacuo. To the resulting thin layer was added 5 mL of an aqueous solution of FD (2 mg/mL). The suspension was passed, at room temperature, through a polycarbonate membrane filter of 0.4 μm for 20 times and then a polycarbonate membrane filter of 0.1 pm for 20 times. An ethanolic solution of PEG-DSPE with a concentration of 1471 mg/mL (0.05 mL) was added thereto followed by heating at 70° C. for 5 minutes, whereupon the surface of the liposome was coated with PEG. The resulting liposome suspension was subjected to a ultracentrifugal separation (110,000×g at 25° C. for 1 hour) and the supernatant liquid was removed. Re-suspending was carried out by adding thereto PBS so as to adjust the total lipid concentration to 30 mg/mL, whereupon a liposome suspension (Preparation e) was obtained.

When an average particle size of the liposome was measured by means of DLS, it was found to be 139 nm.

COMPARATIVE EXAMPLE 6

F-PS was dissolved in PBS whereupon an F-PS solution (Preparation f) was obtained.

COMPARATIVE EXAMPLE 7

Mixing was carried out to prepare DOTAP/PEG-DSPE/distilled water (30 mg/12 mg/mL), followed by shaking and stirring by a vortex mixer. The suspension was passed, at room temperature, through a polycarbonate membrane filter of 0.4 μm for 20 times, a polycarbonate membrane filter of 0.1 μm for 20 times and a polycarbonate membrane filter of 0.05 μm for 20 times. To 0.5 mL of the suspension was added 0.25 mL of an aqueous solution where F-PS was dissolved in distilled water in an amount of 15 mg/mL, whereupon a liposome suspension (Preparation g) in which the total lipid concentration was 28 mg/mL was obtained.

When an average particle size of the liposome was measured by means of DLS, it was found to be 108 nm.

Now the advantages of the present invention will be illustrated by the following Test Examples.

TEST EXAMPLE 1

The preparations 1 to 5 prepared in Examples 1 to 5 and the preparations a to e prepared in Comparative Examples 1 to 5 were subjected to an ultracentrifugal separation (110,000×g at 25° C. for 1 hour). In order to determine the quantity of the FD in each preparation and the FD in the supernatant liquid after the ultracentrifugal separation, fluorescent intensity at excitation wavelength of 485 nm and fluorescence wavelength of 530 nm was measured using a fluorescent microplate reader. Further, phosphatidylcholine (PC) in liposome of each preparation was quantified by means of an enzymatic method using a Phospholipid C Test Wako (manufactured by Wako Pure Chemical). Total lipid concentration was calculated based on the PC concentration in view of a laid-in rate. Enclosing efficiency of FD into liposome per lipid and enclosing rate by ultracentrifugal separation were calculated by the following expressions (1) and (2).

Enclosing efficiency per Lipid (mg FD/mg total lipid)=$(A^1-C^1)/B^1$ (1)

in which
$A^1$: amount of FD in each preparation (mg/mL)
$B^1$: amount of total lipid in each preparation (mg/mL)
$C^1$: amount of FD in the supernatant liquid (mg/mL)

Enclosing Rate by Ultracentrifugal Separation (%)= $[(A^1-C^1)\div B^1]/(D^1\div E^1)\times 100$ (2)

in which
$A^1$: amount of FD in each preparation (mg/mL)
$B^1$: amount of total lipid in each preparation (mg/mL)
$C^1$: amount of FD in the supernatant liquid (mg/mL)
$D^1$: laid-in amount of FD (mg/mL) in Examples 1 to 5 or in Comparative Examples 1 to 5
$E^1$: laid-in amount of total lipid (mg/mL) in Examples 1 to 5 or in Comparative Examples 1 to 5

The result is shown in Table 1 and Table 2.

TABLE 1

Enclosing Efficiency per Lipid

| | Enclosing Efficiency (mg FD/mg total lipid) |
|---|---|
| Preparation 1 | 0.015 |
| Preparation 2 | 0.031 |
| Preparation 3 | 0.063 |
| Preparation 4 | 0.019 |
| Preparation 5 | 0.027 |
| Preparation a | 0.021 |
| Preparation b | 0.009 |
| Preparation c | 0.036 |
| Preparation d | 0.011 |
| Preparation e | 0.007 |

TABLE 2

Enclosing Rate by Ultracentrifugal Separation

| | Enclosing Rate (%) |
|---|---|
| Preparation 1 | 54 |
| Preparation 2 | 72 |
| Preparation 3 | 97 |
| Preparation 4 | 72 |
| Preparation 5 | 81 |
| Preparation a | 70 |
| Preparation b | 36 |
| Preparation c | 12 |
| Preparation d | 38 |
| Preparation e | 26 |

Table 1 shows that the liposomes of the preparations 1 to 5 have high enclosing efficiency as same as those of preparations a and c, however the (amount of FD)/(total lipid amount) in a laying-in stage is not taken into consideration. The laid-in amounts in the manufacture of the preparations 1 to 5 and the preparations a to e are different and, since large amount of FD for the lipid is used for the manufacture particularly in the case of the preparation c, it can be said that the liposomes of the preparations 1 to 5 and the preparation a are the liposome where the amount of FD for the total lipid amount is large when the laid-in amount is taken into consideration.

The enclosing rate as shown in Table 2 is the percentage obtained by dividing the result of Table 1 by (amount of FD)/(total lipid amount) in a laying-in stage, and it reflects the (amount of FD)/(total lipid amount) in a laying-in stage. Table 2 shows that enclosing rate of FD is high in the liposomes of the preparations 1 to 5 and a, while the enclosing rate is low in the liposomes of the preparations b to e. This means that, in the liposomes of the preparations b to e, there are many free FD which is not enclosed and, during the preparing process and analyzing process for enclosing rate, the free FD is removed. From the result, it is understood that, in the laid-in FD, an amount of the FD which is included in the liposome or is mildly bound to (electrostatically adsorbed with) the liposome surface is small and the effectively utilized FD is small in the preparations b to e.

TEST EXAMPLE 2

PBS (1.98 mL) was added to and mixed with each 0.02 mL of the preparations 1 to 5 manufactured in Examples 1 to 5 and the preparations a to e manufactured in Comparative Examples 1 to 5, whereupon a sample solution was produced. Immediately after mixing, 0.5 mL of the sample solution was subjected to gel filtration (Sepharose CL-4B; ø 10 mm×20 cm; mobile phase: PBS; amount of the sample added: 2 mL; amount of fraction collected: about 2 mL). Liposome fraction and a fraction of the component which is not enclosed in the liposome were separated and fluorescence intensity of the eluate was measured by the same manner as in Test Example 1. Enclosing rate by the gel filtration was calculated by the formula (3).

$$\text{Enclosing rate (\%) by the gel filtration} = [F^1/(F^1+G^1)] \times 100 \quad (3)$$

in which
$F^1$: amount of FD in the liposome fraction (mg)
$G^1$: amount of FD in the fraction of the component which is not enclosed in the liposome (mg)
The result is shown in Table 3.

TABLE 3

| Enclosing Rate by Gel Filtration | |
| --- | --- |
| | Enclosing Rate (%) |
| Preparation 1 | 61 |
| Preparation 2 | 71 |
| Preparation 3 | 75 |
| Preparation 4 | 65 |
| Preparation 5 | 55 |
| Preparation a | 13 |
| Preparation b | 16 |
| Preparation c | 82 |
| Preparation d | 26 |
| Preparation e | 70 |

In the gel filtration, not only free FD but also FD which is gently bound to (electrostatically adsorbed with) the surface of liposome are removed. Further, when the stability of the preparation is poor, a part of FD existing in the inner aqueous phase leaks out. Table 3 shows that the enclosing rates of liposome in the preparations 1 to 5, c and e are high. This means FD is abundantly present in the inner aqueous phase of the liposome. However, in Table 3, (amount of FD)/(amount of total lipid) in a laying-in stage is not taken into consideration and, in the preparation c, manufacturing is done using a lot of FD for the lipid, whereby the enclosing rate is naturally high. On the other hand, in the preparations a, b and d, the values are low and FD is not substantially included in the liposome, whereby it can be said that they are the preparations having poor stability.

Table 2 shows a manufacturing property, while Table 3 shows the stability of liposome. From Table 2 and Table 3, it is apparent that the preparation a has a good manufacturing property but is not well stable and, on the contrary, the preparations c and e are stable but manufacturing property is poor. Furthermore, it is apparent that the preparations b and d have poor manufacturing property and stability, while the preparations 1 to 5 have good manufacturing property and stability. That shows that FD is substantially enclosed inside the liposome or, in other words, the FD-cationic lipid complex is coated with lipid in the preparations 1 to 5.

TEST EXAMPLE 3

The preparation 6 prepared in Example 6 was subjected to an ultracentrifugal separation (110,000×g at 25° C. for 1 hour). In order to determine the quantity of the F-Ins in the preparation 6 and the F-Ins in the supernatant liquid after the ultracentrifugal separation, fluorescent intensity at excitation wavelength of 485 nm and fluorescence wavelength of 530 nm was measured using a fluorescent microplate reader. Further, PC in liposome of the preparation was quantified by means of an enzymatic method using a Phospholipid C-Test Wako (manufactured by Wako Pure Chemical). Total lipid concentration was calculated based on the PC concentration in view of a laid-in rate. Enclosing efficiency of F-Ins into liposome per lipid and enclosing rate by ultracentrifugal separation were calculated by the following expressions (4) and (5).

$$\text{Enclosing Efficiency per Lipid (mg F-Ins/mg total lipid)} = (A^2 - C^2)/B^2 \quad (4)$$

in which
$A^2$: amount of F-Ins in the preparation 6 (mg/mL)
$B^2$: amount of total lipid in the preparation 6 (mg/mL)
$C^2$: amount of F-Ins in the supernatant liquid (mg/mL)

$$\text{Enclosing Rate by Ultracentrifugal Separation (\%)} = [(A^2 - C^2) \div B^2]/(D^2 \div E^2) \times 100 \quad (5)$$

in which
$A^2$: amount of F-Ins in the preparation 6 (mg/mL)
$B^2$: amount of total lipid in the preparation 6 (mg/mL)
$C^2$: amount of F-Ins in the supernatant liquid (mg/mL)
$D^2$: laid-in amount of F-Ins (mg/mL) in Example 6
$E^2$: laid-in amount of total lipid (mg/mL) in Example 6
The result is shown in Table 4 and Table 5.

TABLE 4

| Enclosing Efficiency per Lipid | |
| --- | --- |
| | Enclosing Efficiency (mg F-Ins/mg total lipid) |
| Preparation 6 | 0.010 |

TABLE 5

| Enclosing Rate by Ultracentrifugal Separation | |
| --- | --- |
| | Enclosing Rate (%) |
| Preparation 6 | 73 |

Table 4 shows that, in the preparation 6, the enclosing efficiency of F-Ins into the liposome per lipid is high in spite of the fact that the laid-in amount of R-Ins per lipid is small.

With regard to the enclosing rate by ultracentrifugal separation, the measurement is conducted in such a respect that the F-Ins which is gently bound to the liposome surface is enclosed. Table 5 shows that in the liposome of the preparation 6, the enclosing rate is high in the liposome of the preparation 6 as same as in the cases of liposomes of the preparations 1 to 5.

TEST EXAMPLE 4

PBS (1.98 mL) was added to and mixed with 0.02 mL of the preparation 6 manufactured in Example 6, whereupon a sample solution was produced. Immediately after mixing, 0.5 mL of the sample solution was subjected to gel filtration (Sepharose CL-4B; ø 10 mm×20 cm; mobile phase: PBS; amount of the sample added: 2 mL; amount of fraction collected: about 2 mL). Liposome fraction and a fraction of the component which is not enclosed in the liposome were separated and fluorescence intensity of the eluate was measured by the same manner as in Test Example 3. Enclosing rate by the gel filtration was calculated by the formula (6).

$$\text{Enclosing rate (\%) by the gel filtration} = [F^2/(F^2+G^2)] \times 100 \quad (6)$$

in which
$F^2$: amount of F-Ins in the liposome fraction (mg)
$G^2$: amount of F-Ins in the fraction of the component which is not enclosed in the liposome (mg)
The result is shown in Table 6:

TABLE 6

| Enclosing Rate by Gel Filtration | |
|---|---|
| | Enclosing Rate (%) |
| Preparation 6 | 73 |

Enclosing rate by gel filtration is measured after removal of F-Ins which is gently bound to the liposome surface. Table 6 shows that, in the case of liposome of the preparation 6, enclosing rate is high and F-Ins is abundantly present in the inner aqueous phase of the liposome as same as in the cases of the preparations 1 to 5. Thus, it can be said that the preparation 6 is a preparation having good stability where F-Ins is substantially included in the liposome, showing that a complex of F-Ins with lipid is coated with lipid.

TEST EXAMPLE 5

The preparations 7 to 13 prepared in Examples 7 to 13 were subjected to an ultracentrifugal separation (110,000×g at 25° C. for 1 hour). In order to determine the quantity of the F-PS in each preparation and the F-PS in the supernatant liquid after the ultracentrifugal separation, fluorescent intensity at excitation wavelength of 485 nm and fluorescence wavelength of 530 nm was measured using a fluorescent microplate reader. Further, PC in liposome of each preparation was quantified by means of an enzymatic method using a Phospholipid C-Test Wako (manufactured by Wako Pure Chemical). Total lipid concentration was calculated based on the PC concentration in view of a laid-in rate. Enclosing efficiency of F-PS into liposome per lipid and enclosing rate by ultracentrifugal separation were calculated by the following expressions (7) and (8).

$$\text{Enclosing Efficiency per Lipid (mg } F\text{-}PS/\text{mg total lipid)} = (A^3-C^3)/B^3 \quad (7)$$

in which
$A^3$: amount of F-PS in each preparation (mg/mL)
$B^3$: amount of total lipid in each preparation (mg/mL)
$C^3$: amount of F-PS in the supernatant liquid (mg/mL)

$$\text{Enclosing Rate by Ultracentrifugal Separation (\%)} = [(A^3-C^3) \div B^3]/(D^3 \div E^3) \times 100 \quad (8)$$

in which
$A^3$: amount of F-PS in each preparation (mg/mL)
$B^3$: amount of total lipid in each preparation (mg/mL)
$C^3$: amount of F-PS in the supernatant liquid (mg/mL)
$D^3$: laid-in amount (mg/mL) of F-PS in Examples 7 to 13
$E^3$: laid-in amount (mg/mL) of total lipid in Examples 7 to 13
The result is shown in Table 7 and Table 8.

TABLE 7

| Enclosing Efficiency per Lipid | |
|---|---|
| | Enclosing Efficiency (mg F-PS/mg total lipid) |
| Preparation 7 | 0.058 |
| Preparation 8 | 0.034 |
| Preparation 9 | 0.031 |
| Preparation 10 | 0.050 |
| Preparation 11 | 0.059 |
| Preparation 12 | 0.030 |
| Preparation 13 | 0.024 |

TABLE 8

| Enclosing Rate by Ultracentrifugal Separation | |
|---|---|
| | Enclosing Rate (%) |
| Preparation 7 | 109 |
| Preparation 8 | 126 |
| Preparation 9 | 76 |
| Preparation 10 | 107 |
| Preparation 11 | 111 |
| Preparation 12 | 86 |
| Preparation 13 | 97 |

Table 7 shows that, in the preparations 7 to 13, the enclosing efficiency of F-PS per lipid is high.

In the enclosing rate by ultracentrifugal separation, the measurement is conducted in such a respect that the F-PS which is gently bound to the liposome surface is also enclosed. Table 8 shows that the liposomes of the preparations 7 to 13 are liposomes where the enclosing rate of F-PS is high.

TEST EXAMPLE 6

PBS (1.98 mL) was added to and mixed with 0.02 mL of the preparations 7 to 9, 11 and 12 manufactured in Examples 7 to 9, 11 and 12, whereupon a sample solution was produced. Immediately after mixing, 0.5 mL of the sample solution was subjected to gel filtration (Sepharose CL-4B; ø 10 mm×20 cm; mobile phase: PBS; amount of the sample added: 2 mL; amount of fraction collected: about 2 mL). Liposome fraction and a fraction of the component which is not enclosed in the liposome were separated and fluorescence intensity of the eluate was measured by the same manner as in Test Example 5. Enclosing rate by the gel filtration was calculated by the formula (9).

$$\text{Enclosing rate (\%) by the gel filtration} = [F^3/(F^3+G^3)] \times 100 \quad (9)$$

in which
$F^3$: amount of F-PS in the liposome fraction (mg)
$G^3$: amount of F-PS in the fraction of the component which is not enclosed in the liposome (mg)
The result is shown in Table 9.

TABLE 9

| Enclosing Rate by Gel Filtration | |
|---|---|
| | Enclosing Rate (%) |
| Preparation 7 | 84 |
| Preparation 8 | 96 |
| Preparation 9 | 94 |
| Preparation 11 | 90 |
| Preparation 12 | 89 |

Enclosing rate by gel filtration was measured after removal of F-PS which is gently bound to the liposome surface. Table 9 shows that, in the case of liposome of the preparations 7 to 9, 11 and 12, enclosing rate is high and F-PS is abundantly present in the inner aqueous phase of the liposome. Thus, it can be said that the preparations 7 to 9, 11 and 12 are the preparations having good stability where F-PS is substantially included in the liposome, showing that a complex of F-PS with lipid is coated with lipid.

TEST EXAMPLE 7

Comparison was made to investigate distribution of F-PS to tumor. Tumor piece of 2 mm square from human renal cancer cell Caki-1 was transplanted under the skin of right body of six-week old nude mouse (CLEA Japan) of a BALE/cA Jcl-nu strain. After 20 days from the transplantation, mice in which tumor volume reached 102 to 349 mm$^3$ were grouped in such a manner that each group comprised 3 mice, and the preparation 7 manufactured in Example 7 and the preparation f manufactured in Comparative Example 6 each was administered from tail vein of the mouse using a syringe (26 G; 1 mL; manufactured by Terumo) at the dose of 25 mg F-PS/kg. Tumor was excised from time to time, the tumor was homogenized and the fluorescence intensity in the homogenate was measured by the same manner as in Test Example 5. Distribution of F-PS to tumor was evaluated by calculating the F-PS amount in tumor (µg/g) at each time point.

The result is shown in FIG. 2.

FIG. 2 shows that, in the mice to which the preparation 7 was administered, the amount of F-PS distributed to tumor increases as compared with the mice to which the preparation f was administered.

TEST EXAMPLE 8

The preparation 1 manufactured in Example 1 was subjected to a morphological observation using electron microscope. The preparation was added to a 1% aqueous solution of ammonium molybdate (adjusted to pH 7.3 using ammonia) so as to adjust the total lipid concentration to 0.5 mg/mL. This was dropped onto a mesh (400 mesh; Nisshin EM) to which collodion membrane was attached and, after about 1 minute, excessive water was absorbed with filter paper followed by drying. An observation was made using a transmission electron microscope (type H-7000; Hitachi) with an accelerating voltage of 75 kV.

The result was that, in the preparation 1, there were a lot of particles having therein particle whose form is different from that of the membrane which surrounded the outside. Thus, this result shows that the inner particles are coated with a lipid bilayer.

TEST EXAMPLE 9

The preparation 1 manufactured in Example 1 and the preparations a and b manufactured in Comparative Examples 1 and 2 were administered (dose: corresponding to 10 mg of total lipid per kg) to CD(SD)IGS male rats under urethane anesthetization (body weight: 200 to 300 g; one group comprised 2 or 3 rats) from the femoral vein. Blood was collected from time to time using a heparin-treated syringe from the jugular vein and centrifuged (10,000×g at 4° C. for 5 minutes). Thereafter, the fluorescent intensity of FD in the plasma was measured by the same manner as in Test Example 1 and FD concentration in the plasma was calculated.

The result is shown in FIG. 3.

FIG. 3 shows that, in the rats to which the preparation 1 was administered, level in the concentration of FD in the plasma was high as compared with the rats to which the preparation a or b was administered. Thus, it is shown that, due to the coating of FD-lipid complex with lipid, retention in blood is improved.

TEST EXAMPLE 10

The preparations 7 to 13 manufactured in Examples 7 to 13 and the preparation f manufactured in Comparative Example 6 were administered (does: corresponding to 10 mg of the total lipid per kg) to CD(SD)IGS male rats (body weight: 200 to 300 g; one group comprised 2 rats) under urethane anesthetization from the femoral vein. Blood was collected from time to time using a heparin-treated syringe from the jugular vein and centrifuged (10,000×g at 4° C. for 5 minutes). Thereafter, the fluorescent intensity of F-PS in the plasma was measured by the same manner as in Test Example 5 and F-PS concentration in the plasma was calculated.

The result is shown in FIG. 4.

FIG. 4 shows that, in the rats to which the preparations 7 to 13 were administered, the level in the concentration of F-PS in the plasma was high as compared with the rats to which the preparation f was administered.

TEST EXAMPLE 11

The preparation 7 manufactured in Example 7 and the preparations f to g manufactured in Comparative Examples 6 to 7 were administered (dose: corresponding to 10 mg of total lipid per kg) to BALB/cA Jcl male mice (body weight: 20 to 30 g; one group comprised 2 or 3 mice) from the tail vein. Under ether anesthetization, blood was collected from femoral vein using a heparin-treated syringe and centrifuged (10,000×g at 4° C. for 5 minutes). Thereafter, fluorescence intensity of F-PS in the plasma was measured by the same manner as in Test Example 5 and F-PS concentration in the plasma was calculated.

The result is shown in FIG. 5.

FIG. 5 shows that, in the mice to which the preparations f to g were administered, F-PS quickly disappeared from the plasma after its administration, while in the mice to which the preparation 7 was administered, the level in the concentration of F-PS in the plasma was high.

TEST EXAMPLE 12

The preparations 13 to 18 manufactured in Examples 13 to 18 were subjected to ultracentrifugal separation (110,000×g at 25° C. for 1 hour). In order to determine the quantity of the F-PS in each preparation and the F-PS in the supernatant liquid after the ultracentrifugal separation, fluorescent intensity at excitation wavelength of 485 nm and fluorescence wavelength of 530 nm was measured using a fluorescent microplate reader. Enclosing rate of F-PS to liposome by ultracentrifugal separation was calculated by the following expression (10).

Enclosing Rate by Ultracentrifugal Separation (%)=
$[(A^4-B^4)]/B^4 \times 100$ (10)

$A^4$: amount of F-PS in each preparation (mg/mL)
$B^4$: amount of F-PS in the supernatant liquid (mg/mL)
The result is shown in Table 10.

TABLE 10

Enclosing Rate by Ultracentrifugal Separation

|  | Enclosing Rate (%) |
|---|---|
| Preparation 13 | 98 |
| Preparation 14 | 95 |
| Preparation 15 | 97 |
| Preparation 16 | 98 |
| Preparation 17 | 95 |
| Preparation 18 | 99 |

TEST EXAMPLE 13

Fetal Bovine serum (FBS) (7.92 mL) was added to and mixed with each 0.08 mL of the preparations 7 and 14 to 18 manufactured in Examples 7 and 14 to 18, whereupon a sample solution was produced. Immediately after mixing (0 hour) and after being allowed to stand at 37° C. for 6 to 168 hours, samplings were conducted and 0.5 mL of each of the sample solutions was subjected to gel filtration (Sepharose CL-4B; ø 10 mm×20 cm; mobile phase: PBS; amount of the sample added: 2 mL; amount of fraction collected: about 2 mL). Liposome fraction and a fraction of the component which was not enclosed in the liposome were separated. In order to quantify the F-PS in each fraction, fluorescence intensity at excitation wavelength of 485 nm and fluorescence wavelength of 530 nm was measured using a fluorescent microplate reader. Amount of F-PS leaked out from the liposome was calculated by the expression (11).

$$\text{Amount of F-PS leaked out (\%)} = [B^5/(A^5+B^5)] \times 100 \qquad (11)$$

$A^5$: amount of F-PS in the lipbsome fraction (mg)
$B^5$: amount of F-PS in the component which is not enclosed in the liposome (mg)
The result is shown in Table 11.

TABLE 11

Leakage of F-PS from Liposome in FBS (% Leakage)

| Time (Hour(s)) | 0 | 6 | 24 | 48 | 72 | 96 | 168 |
|---|---|---|---|---|---|---|---|
| Preparation 7 | 17 | 28 | 41 | 51 | 52 | — | 64 |
| Preparation 14 | 30 | 47 | 55 | 63 | 62 | — | 65 |
| Preparation 15 | 35 | 48 | 54 | 57 | — | — | 72 |
| Preparation 16 | 29 | 44 | 56 | 55 | — | — | 62 |
| Preparation 17 | 15 | 21 | 26 | — | — | 43 | 47 |
| Preparation 18 | 27 | 43 | 51 | 55 | — | — | 57 |

Table 11 shows the F-PS in the preparations 7 and 14 to 18 leaks from the liposome with a lapse of time. Thus, when the fine particles are coated with lipid membrane using the method of the present invention, fine particles of a drug or the like enclosed in the lipid membrane are leaked out after accumulating at the target site in the body, whereupon achievement of sustained pharmaceutical effect is now possible.

TEST EXAMPLE 14

Gel filtration of the preparations 19 to 21 manufactured in Examples 19 to 21 was carried out. A liposome suspension (0.5 mL) was used as a sample solution and added to a gel filtration column (Sepharose CL-4B; ø 10 mm×20 cm; mobile phase: PBS; amount of the sample added: 0.5 mL; amount of the fraction collected: about 1.5 mL). Liposome fraction and free G-CSF fraction were separated, and each of them was concentrated by means of a centrifugal evaporation. Distilled water was added to the concentrated liposome fraction to make the total volume 2 mL. To 200 µL of the liposome suspension were added 50 µL of a 50 mmol/L phosphate buffer of pH 7 containing 10% of sodium laurylsulfate and 150 µL of distilled water, followed by stirring. Further, 400 µL of 2-propanol was added thereto followed by stirring so that liposome was completely destroyed, and then 800 µL of the following mobile phase I was added thereto and mixed. A centrifugal separation (10,000×g for 5 minutes) was carried out and the supernatant liquid was subjected to an HPLC analysis. To the concentrated free G-CSF fraction were added a 50% aqueous solution of acetonitrile containing 2% of Pluronic F 127 (manufactured by Sigma) and 0.5% of trifluoroacetic acid (TFA) so as to make the total volume 5 mL, which was then subjected to an HPLC analysis.

Column: YMCpack ODS-AM, ø6.0 mm×15 cm
Mobile phase: I 50% acetonitrile containing 0.5% TFA II 80% acetonitrile containing 0.5% TFA
Rate of the liquid II after initiation of the analysis was made 0% during 0 to 5 minute(s), linearly increased within 0% to 100% during 5 to 35 minutes and made 100% during 35 to 45 minutes.
Detection: 280 nm
Temperature for analysis: 30° C.
Flow rate: 1 mL/minute
Injected amount: 200 µL
Enclosing rate of G-CSF enclosed in each liposome was calculated by the expression (12).

$$\text{Enclosing Rate (\%)} = A^6/(A^6+B^6) \times 100 \qquad (12)$$

$A^6$: amount of G-CSF in liposome fraction (µg)
$B^6$: amount of G-CSF in free G-CSF fraction (µg)
The result is shown in Table 12.

TABLE 12

Enclosing Rate

|  | Enclosing Rate (%) |
|---|---|
| Preparation 19 | 100 |
| Preparation 20 | 100 |
| Preparation 21 | 100 |

Table 12 shows that the preparations 19 to 21 are those where no free G-CSF separated by gel filtration is contained therein.

INDUSTRIAL APPLICABILITY

In accordance with the present invention, safe, convenient and efficient coating of fine particles with lipid membrane is now possible.

The invention claimed is:
1. A coated fine particle comprising:
  (i) a complex containing a drug, a cationic lipid, and a water-soluble polymer derivative,
    wherein the drug is a nucleic acid and the complex is obtained by mixing the drug, the water-soluble polymer derivative, and the cationic lipid in water,
    wherein the complex has a diameter of 10 nm to 1,000 nm, and wherein the water-soluble polymer derivative is one or more member(s) selected from a copolymer of ethylene glycol with propylene glycol, and a glycerol ester, and (ii) a lipid membrane formed of lipid(s), wherein the lipid(s) is selected from phosphatidylserine, phosphatidylglycerol, lysophosphatidylcholine, polyethylene glycolated phospholipid, egg yolk lecithin, soybean lecithin and hydrogenated phospholipid, and wherein the complex is coated with the lipid membrane.

* * * * *